United States Patent
Yoshimoto et al.

(10) Patent No.: US 7,771,842 B2
(45) Date of Patent: Aug. 10, 2010

(54) 1,4-BENZODIOXANE SULFONIC ACID COMPOUND AND USE THEREOF AS ELECTRON-ACCEPTOR MATERIAL

(75) Inventors: Takuji Yoshimoto, Funabashi (JP); Tomohisa Yamada, Funabashi (JP)

(73) Assignee: Nissan Chemical Industries, Ltd., Tokyo (JP)

(*) Notice: Subject to any disclaimer, the term of this patent is extended or adjusted under 35 U.S.C. 154(b) by 1204 days.

(21) Appl. No.: 10/562,065

(22) PCT Filed: Jun. 23, 2004

(86) PCT No.: PCT/JP2004/009210
§ 371 (c)(1), (2), (4) Date: Dec. 22, 2005

(87) PCT Pub. No.: WO2005/000832
PCT Pub. Date: Jan. 6, 2005

(65) Prior Publication Data
US 2007/0105030 A1 May 10, 2007

(30) Foreign Application Priority Data
Jun. 25, 2003 (JP) .............................. 2003-181025

(51) Int. Cl.
*B32B 9/00* (2006.01)
*G02B 5/30* (2006.01)
*C07D 319/14* (2006.01)

(52) U.S. Cl. .................. 428/690; 359/494; 549/362

(58) Field of Classification Search ................ 549/362; 359/494; 428/690
See application file for complete search history.

(56) References Cited

U.S. PATENT DOCUMENTS 5,387,681 A  2/1995  Miller et al.
5,602,260 A * 2/1997  Blakeney et al. ............ 549/362

FOREIGN PATENT DOCUMENTS

| FR | 2747678 A1 | 10/1997 |
|---|---|---|
| JP | 6-199825 A | 7/1994 |
| JP | 2001-106782 A | 4/2001 |
| JP | 2002-151272 A | 5/2002 |
| JP | 2003-338379 A | 11/2003 |

OTHER PUBLICATIONS

C. W. Tang et al., Applied Physics Letters, U.S., vol. 51, (12), Sep. 21, 1987, p. 913 to 915.
J. H. Burroughes et al., Nature, England, vol. 347, Oct. 11, 1990, p. 539 to 541.
S. A. Van Slyke et al., Applied Physics Letters, U.S., vol. 69, Oct. 7, 1996, p. 2160 to 2162.
G. Gustafsson et al., Nature, England, vol. 357, Jun. 11, 1992, p. 477 to 479.
Y. Yang et al., Applied Physics Letters, U.S., vol. 64 (10) Mar. 7, 1994, p. 1245 to 1247.
Jayesh Bharathan et al., Applied Physics Letters, U.S., vol. 72 No. 21, May 25, 1998, p. 2660 to 2662.
Takeo Wakimoto et al., IEEE Transactions on Electron Devices, U.S., vol. 44, No. 8, Aug. 1997, p. 1245 to 1248.
L. S. Hung et al., Applied Physics Letters, U.S., vol. 70 (2) Jan. 13, 1997, p. 152 to 154.
Chimed Ganzorig et al., Japanese Journal of Applied Physics, vol. 38 (1999) p. L1348 to L1350.
Juzo Nakayama et al., Heterocycles, vol. 26, No. 4, 1987, p. 939 to 942.
Juzo Nakayama et al., Heterocycles, vol. 26, No. 7, 1987, p. 1793 to 1796.
Miyoko Ochi et al., Bulletin of Chemical Society of Japan, vol. 67, 1994, p. 1749 to 1752.

* cited by examiner

*Primary Examiner*—Janet L. Andres
*Assistant Examiner*—Raymond Covington
(74) *Attorney, Agent, or Firm*—Birch, Stewart, Kolasch & Birch, LLP

(57) ABSTRACT

By using a charge-transporting thin film which is made of charge-transporting varnish containing, as an electron-acceptor material, a 1,4-benzodioxane sulfonic acid compound represented by the formula (1) below especially in an OLED device or a PLED device, there can be realized excellent EL device characteristics such as low driving voltage, high luminous efficiency and long life.

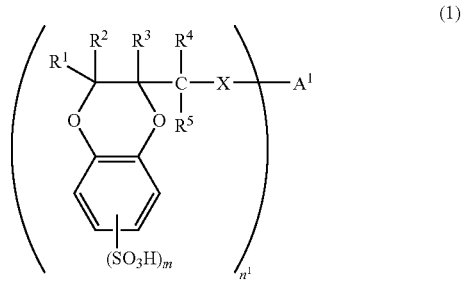

6 Claims, No Drawings

1,4-BENZODIOXANE SULFONIC ACID COMPOUND AND USE THEREOF AS ELECTRON-ACCEPTOR MATERIAL

TECHNICAL FIELD

The present invention relates to a 1,4-benzodioxanesulfonic acid compound and its use as an electron acceptor. The mode of use includes a varnish containing the electron acceptor, a charge transporting thin film formed from the varnish, and an organic electroluminescence (EL for short hereinafter) device having said charge transporting thin film.

BACKGROUND ART

The organic EL device, particularly low-molecular weight organic EL (OLED for short hereinafter) device, has greatly improved in characteristic properties since development by Eastman Kodak Company in the structure of organic layers, such as extremely thin layers and multiple layers for separate functions and substantially reduced driving voltage. (See, for example, Applied Physics Letters, U.S., 1987, vol. 51, p. 913 to 915.)

The recent organic EL device, such as the one based on a polymeric luminescent material (PLED for short hereinafter), which has been developed by Cambridge University, is comparable to the conventional OLED device. (See, for example, Nature, England, 1990, vol. 347, p. 539 to 541.)

On the other hand, it has been reported that the OLED device improves in initial characteristic properties (such as reduced driving voltage and increased light emitting efficiency) and lifetime, if it has a copper phthalocyanine (CuPC) layer as the hole injection layer. (See, for example, Applied Physics Letters, U.S., 1996, vol. 69, p. 2160 to 2162.)

It has also been reported that the PLED device produces the same effect as the OLED device if it has a hole transporting layer (buffer layer) formed from a polyaniline-based material or a polythiophene-based material. (For the former, refer to Nature, England, 1992, vol. 357, p. 477 to 479, and Applied Physics Letters, U.S., 1994, vol 64, p. 1245 to 127. For the latter refer to Applied Physics Letters, U.S., 1998, vol. 72, p. 2660 to 2662.)

In addition, it has been found that an electron injection layer adjacent to the cathode improves the initial characteristic properties. The electron injection layer is formed from any of metal oxide, metal halide, and metal complex, which were reported respectively in IEEE Transaction on Electron Devices, U.S., 1997, vol. 44, p. 1245 to 1248; Applied Physics Letters, U.S., 1997, vol. 70, p. 152 to 154; and Japanese Journal of Applied Physics, 1999, vol. 38, p. L1348 to 1350. These findings led to the common use of charge injection layer and buffer layer.

It has recently been found that the EL device exhibits outstanding characteristic properties if it has a hole injection layer formed from a charge transporting varnish in the form of organic solvent solution of low-molecular weight oligoaniline. (See, for example, Japanese Patent Laid-open No. 2002-151272.)

Unfortunately, CuPC as a common material for the hole injection layer in the OLED device has the disadvantage of greatly deteriorating the characteristic properties when it is added to other organic layers no matter how small its quantity may be because of its large surface irregularities. Moreover, polyaniline- and polythiophene-based materials, which are currently used for the PLED device, involves problems arising from the fact that they contain water as a solvent which accelerates device deterioration, they are limited in solvent selection, and they are limited in method of uniform film forming because of their low solubility and tendency toward aggregation. Even the charge transporting varnish in the form of organic solvent solution containing a highly soluble low-molecular weight oligoaniline-based material is limited in the kind of electron accepting dopant that can be used because most electron accepting dopants are poor in heat resistance and amorphousness. A problem common to the charge transporting varnish containing a low-molecular weight charge transporting substance and a charge accepting dopant substance, particularly the varnish containing a crystalline substance, is that they usually present difficulties in forming a perfectly flat film.

DISCLOSURE OF THE INVENTION

The present invention was completed in view of the foregoing. It is an object of the present invention to provide a 1,4-benzodioxanesulfonic acid compound as an electron acceptor substance to be applied to OLED devices and PLED devices for their improved characteristic properties, such as low driving voltage, high light emitting efficiency, and long lifetime, arising from its ability to form a highly uniform film.

In order to address the above-mentioned problems, the present inventors carried out extensive studies, which led to the finding that the 1,4-benzodioxanesulfonic acid compound represented by formulas (1) to (4) have good heat resistance and high amorphousness and are soluble in an organic solvent, such as N,N-dimethylformamide (DMF for short hereinafter).

It was also found that when combined with a charge transporting host substance, the 1,4-benzodioxanesulfonic acid compound accepts electrons from the host substance, thereby improving in charge transporting performance, with the result that the compound functions as the hole injection layer in OLED devices or the like to reduce driving voltage and increase light-emitting efficiency.

It was also found that the charge transporting thin film exhibits a high degree of amorphousness if it is formed from a combination of the compound and the crystalline charge transporting host substance.

Although organic sulfonic acid compounds do not readily undergo nucleophilic substitution reaction in an ordinary organic solvent on account of their low solubility and hence they cannot be readily made into derivatives, it was found that the compound represented by formula (7) permits the nucleophilic substitution reaction to readily proceed in water alone or in combination with an organic solvent, thereby yielding a 1,4-benzodioxanesulfonic acid compound represented by formula (9).

The present invention covers the following six aspects.

[1] A 1,4-benzodioxanesulfonic acid compound represented by formula (1), a 1,4-benzodioxanesulfonic acid compound represented by formula (2), a 1,4-benzodioxanesulfonic acid compound having the repeating unit represented by formula (3), or a 1,4-benzodioxanesulfonic acid compound having the repeating unit represented by formula (4).

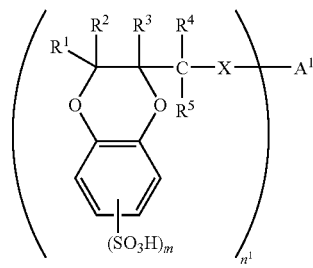

(where $R^1$ to $R^5$ each independently denotes a hydrogen atom, an unsubstituted or substituted monovalent hydrocarbon group, or a halogen atom; X denotes a single bond, O, S, or NH; $A^1$ denotes a hydrogen atom, a halogen atom (if X denotes a single bond), S (if X denotes a single bond), S(O) group, S(O$_2$) group, any of N, Si, P, and P(O) group having an unsubstituted or substituted group binding thereto, an unsubstituted or substituted hydrocarbon group, 1,3,5-triazine group, or a substituted or unsubstituted group represented by formula (5) or (6)

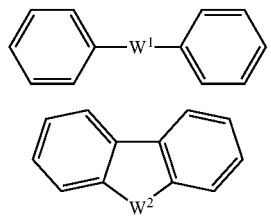

(5)

(6)

(where $W^1$ and $W^2$ each independently denotes O, S, S(O) group, S(O$_2$) group, or any of N, Si, P, and P(O) group having an unsubstituted or substituted group binding thereto); $n^1$ is an integer which equals the valence of $A^1$ and satisfies $1 \leq n^1$; and m denotes the number of sulfonic acid groups binding to the benzene ring of the 1,4-benzodioxane skeleton, with $1 \leq m \leq 4$.)

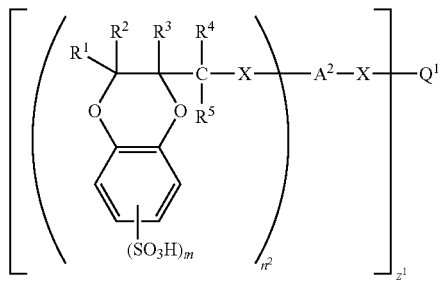

(2)

(where $R^1$ to $R^5$, X, and m are defined as above; $A^2$ denotes an unsubstituted or substituted divalent or higher multi-valent hydrocarbon group, a divalent or trivalent 1,3,5-triazine group, or a substituted or unsubstituted group represented by the formula (5) or (6) above; $Q^1$ denotes a hydrogen atom, a halogen atom (if X denotes a single bond), S (if X denotes a single bond), S(O) group, S(O$_2$) group, any of N, Si, P, and P(O) group having an unsubstituted or substituted group binding thereto, an unsubstituted or substituted hydrocarbon group, 1,3,5-triazine group, or a substituted or unsubstituted group represented by the formula (5) or (6) above; $n^2$ is an integer which equals the number of valence of $A^2$ minus 1 and satisfies $1 \leq n^2$; and $z^1$ is an integer which equals the number of valence of $Q^1$ and satisfies $1 \leq z^1$.)

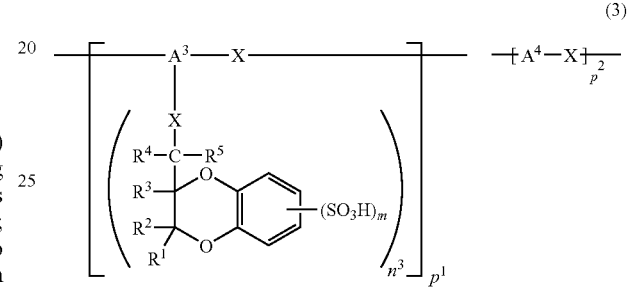

(3)

(where $R^1$ to $R^5$, X, and m are defined as above; $A^3$ denotes an unsubstituted or substituted trivalent or higher multi-valent hydrocarbon group, a trivalent 1,3,5-triazine group, or a substituted or unsubstituted group represented by the formula (5) or (6) above; $A^4$ denotes an unsubstituted or substituted divalent or higher multi-valent hydrocarbon group, a divalent or trivalent 1,3,5-triazine group, or a substituted or unsubstituted group represented by the formula (5) or (6) above; $n^3$ is an integer which equals the number of valence of $A^3$ minus 2 and satisfies $1 \leq n^3$; and $p^1$ is an integer which satisfies $1 \leq p^1$ and $p^2$ is an integer which satisfies $0 \leq p^2$, with $1 \leq p^1 + p^2 \leq 10000$.)

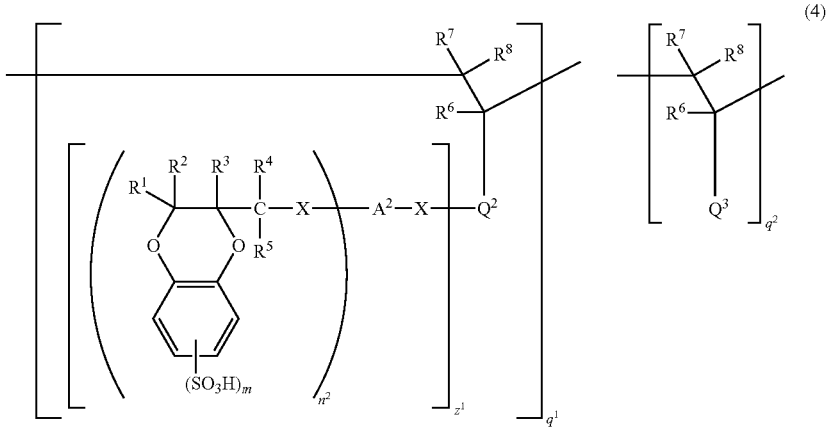

(4)

(where $R^1$ to $R^5$, $A^2$, X, m, and $n^2$ are defined as above; $R^6$ to $R^8$ each independently denotes a hydrogen atom, an unsubstituted or substituted monovalent hydrocarbon group, or a halogen atom; $Q^2$ denotes an unsubstituted or substituted divalent or higher multi-valent hydrocarbon group, a divalent or trivalent 1,3,5-triazine group, or a substituted or unsubstituted group represented by the formula (5) or (6) above; $Q^3$ denotes an unsubstituted or substituted hydrocarbon group, a 1,3,5-triazine group, or a substituted or unsubstituted group represented by the formula (5) or (6) above; $z^2$ is an integer which equals the number of valence of $Q^2$ minus 1 and satisfies $1 \leq z^2$; and $q^1$ is an integer which satisfies $1 \leq q^1$ and $q^2$ is an integer which satisfies $0 \leq q^2$, with $1 \leq q^1 + q^2 \leq 10000$.)

[2] An electron acceptor substance composed of the 1,4-benzodioxanesulfonic acid compound as defined in [1].

[3] A charge transporting varnish comprising the 1,4-benzodioxanesulfonic acid compound as defined in [1], a charge transporting substance, and a solvent.

[4] A charge transporting thin film comprising the 1,4-benzodioxanesulfonic acid compound as defined in [1] and a charge transporting substance.

[5] An organic electroluminescence device having the charge transporting thin film as defined in [4].

[6] A process which comprises reacting (o-dihydroxybenzene) sulfonic acid represented by formula (7)

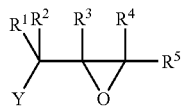

(7)

(where m denotes the number of sulfonic acid groups binding to the hydroxybenzene ring, with $1 \leq m \leq 4$.)

with an epihalohydrin compound represented by formula (8)

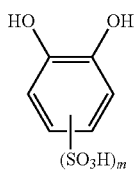

(8)

(where $R^1$ to $R^5$ each independently denotes a hydrogen atom, an unsubstituted or substituted monovalent hydrocarbon group, or a halogen atom; and Y denotes a halogen atom.)

in the presence of a catalyst, thereby producing a 1,4-benzodioxanesulfonic acid compound represented by formula (9)

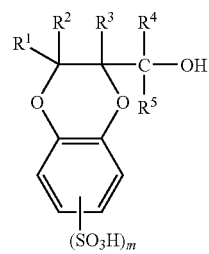

(9)

(where $R^1$ to $R^5$ and m are defined as above.)

The 1,4-benzodioxanesulfonic acid compound according to the present invention is amorphous and highly soluble in organic solvents. It is used as a dopant for a charge transporting varnish of organic solvent solution type, which gives an amorphous solid thin film. The thin film containing the 1,4-benzodioxanesulfonic acid compound is used as the hole injection layer or hole transporting layer in an organic EL device, so as to lower the driving voltage, increase the light-emitting current efficiency, and produce a uniform light-emitting surface. In addition, it is soluble in an organic solvent, unlike the conventional charge transporting varnish of aqueous solution type, and this offers the advantage of protecting the EL device from deterioration by water.

The charge transporting varnish of organic solvent solution type, which contains 1,4-benzodioxanesulfonic acid compound according to the present invention, will be used to form capacitor electrode protective film or antistatic film.

BEST MODE FOR CARRYING OUT THE INVENTION

The following is a detailed description of the invention.

The 1,4-benzodioxanesulfonic acid compound represented by formulas (1) to (4) is not specifically restricted so long as it contains $R^1$ to $R^8$ each independently denoting a hydrogen atom, an unsubstituted or substituted monovalent hydrocarbon group, or a halogen atom.

Examples of the monovalent hydrocarbon group include alkyl groups (such as methyl group, ethyl group, n-propyl group, i-propyl group, n-butyl group, i-butyl group, t-butyl group, n-hexyl group, n-octyl group, 2-ethylhexyl group, and decyl group), cycloalkyl groups (such as cyclopentyl group and cyclohexyl group), bicycloalkyl groups (such as bicyclohexyl group), alkenyl groups (such as vinyl group, 1-propenyl group, 2-propenyl group, isopropenyl group, 1-methyl-2-propenyl group, 1-, 2-, or 3-butenyl group, and hexenyl group), aryl groups (such as phenyl group, xylyl group, tolyl group, biphenyl group, and naphthyl group), and aralkyl groups (such as benzyl group, phenylethyl group, and phenylcyclohexyl group). The monovalent hydrocarbon group may have its hydrogen atoms replaced partly or entirely by halogen atoms, hydroxyl groups, alkoxyl groups, or sulfonic acid groups.

Preferred examples of $R^1$ to $R^8$ include hydrogen atoms, methyl groups, ethyl groups, i-propyl groups, t-butyl groups, 2-ethylhexyl groups, fluorine atoms, and chlorine atoms.

In formulas (1) to (4), X denotes a single bond, O, S, or NH, with O being preferable. Incidentally, "single bond" means that atoms or atomic groups adjacent to X bind directly each other.

$A^1$ and $Q^1$ each denotes a hydrogen atom, a halogen atom (if X denotes a single bond), S (if X denotes a single bond), S(O) group, $S(O_2)$ group, any of N, Si, P, and P(O) group having an unsubstituted or substituted group binding thereto, an unsubstituted or substituted hydrocarbon group, 1,3,5-triazine group, or a substituted or unsubstituted group represented by formula (5) or (6) below

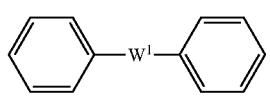

(5)

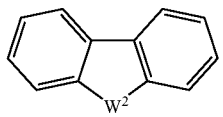

(where $W^1$ and $W^2$ each independently denotes O, S, S(O) group, S(O$_2$) group, or any of N, Si, P, and P(O) group having an unsubstituted or substituted group binding thereto.) Incidentally, "unsubstituted" means the binding of a hydrogen atom. Any of the following is desirable from the standpoint of improved durability and improved charge transporting characteristics. A hydrogen atom, a divalent or higher multi-valent unsubstituted or substituted hydrocarbon group containing at least one aromatic ring, a divalent or trivalent 1,3,5-triazine group, and a substituted or unsubstituted divalent diphenylsulfone group. Any of the following is more desirable. A hydrogen atom, a divalent or trivalent substituted or unsubstituted benzyl group, a divalent substituted or unsubstituted p-xylylene group, a divalent or trivalent substituted or unsubstituted naphthyl group, a divalent or trivalent 1,3,5-triazine group, a divalent substituted or unsubstituted diphenylsulfone group, a di- to tetravalent perfluorobiphenyl group, a divalent substituted or unsubstituted 2,2-bis((hydroxypropoxy)phenyl)propyl group, and a substituted or unsubstituted polyvinylbenzyl group.

$n^1$ denotes the number of valence of $A^1$; it is not specifically restricted so long as it is an integer that satisfies $1 \leq n^1$.

m denotes the number of sulfonic acid groups binding to the benzene ring of the 1,4-benzodioxane skeleton; it is not specifically restricted so long as it satisfies $1 \leq m \leq 4$. The value of m should preferably be 1 or 2 from the standpoint of high solubility and high electron accepting performance.

$A^2$, $A^3$, $A^4$, $Q^2$, and $Q^3$, each representing an unsubstituted or substituted hydrocarbon group, are not specifically restricted; however, for improved durability and improved charge transporting performance, they should preferably be a hydrocarbon group containing at least one aromatic ring, such as unsubstituted benzyl group, substituted or unsubstituted p-xylylene group, substituted or unsubstituted naphthyl group, perfluorobiphenyl group, 2,2-bis-((hydroxypropoxy)phenyl)propyl group, and substituted or unsubstituted polyvinyl benzyl group. They should have the specified number of valance.

$A^2$, $A^3$, $A^4$, $Q^2$, and $Q^3$, each representing an unsubstituted or substituted group represented by formula (5) or (6), are not specifically restricted; however, they should preferably be a diphenylsulfone group having the specified number of valence as in the case of $A^1$ and $Q^1$.

$n^2$ is not specifically restricted so long as it is an integer which equals (the number of valence of $A^2$ minus 1) and satisfies $1 \leq n^2$.

$n^3$ is not specifically restricted so long as it is an integer which equals (the number of valence of $A^3$ minus 2) and satisfies $1 \leq n^3$.

$p^1$ is an integer which satisfies $1 \leq p^1$, and $p^2$ is an integer which satisfies $0 \leq p^2$, with $1 \leq p^1+p^2 \leq 10000$, preferably $1 \leq p^1+p^2 \leq 5000$.

$q^1$ is an integer which satisfies $1 \leq q^1$, and $q^2$ is an integer which satisfies $0 \leq q^2$, with $1 \leq q^1+q^2 \leq 10000$, preferably $1 \leq q^1+q^2 \leq 5000$.

$z^1$ is not specifically restricted so long as it is an integer which equals the number of valence of $Q^2$ and satisfies $1 \leq z^1$.

$z^2$ is not specifically restricted so long as it is an integer which equals (the number of valence of $Q^2$ minus 1) and satisfies $1 \leq z^2$.

The 1,4-benzodioxanesulfonic acid compound, which is represented by formulas (1) to (4), may be prepared by the following method.

That is, (o-dihydroxybenzene) sulfonic acid (as the starting material) represented by formula (7)

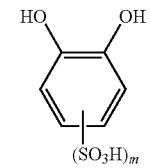

(where m is defined as above)

is converted into a 1,4-benzodioxanesulfonic acid compound represented by formula (10)

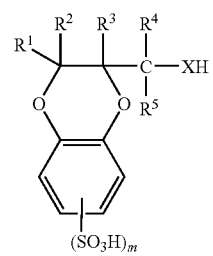

(where $R^1$ to $R^5$, X, and m are defined as above.)

A 1,4-benzodioxanesulfonic acid compound represented by formula (10), in which X denotes an oxygen atom, may be prepared by reacting the (o-dihydroxybenzene) sulfonic acid represented by formula (7) above with an epihalohydrin compound represented by formula (8)

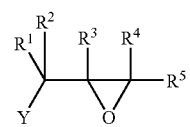

(where $R^1$ to $R^5$ and Y are defined as above) in the presence of a catalyst, thereby giving the desired 1,4-benzodioxanesulfonic acid compound represented by formula (9)

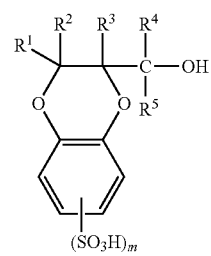

(where $R^1$ to $R^5$ and m are defined as above.)

The (o-dihydroxybenzene)sulfonic acid represented by formula (7) may be preferably used in the form of the sulfonate, such as, for example, 4,5-dihydroxy-1,3-benzenedisulfonate represented by formula (11).

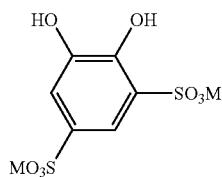

(11)

(where M denotes an alkali metal such as Na and K.)

The epihalohydrin compound represented by formula (8) as another raw material is not specifically restricted. Its preferred examples include epifluorohydrin, epichlorohydrin, epibromohydrin, and epithiochlorohydrin. These epihalohydrin compounds should preferably be used 0.8 to 1.5 times (in mole) as much as the 4,5-dihydroxy-1,3-benzenedisulfonate represented by formula (11) above.

The catalyst includes inorganic bases (such as sodium carbonate, potassium carbonate, cesium carbonate sodium hydrogen carbonate, potassium hydrogen carbonate, lithium hydroxide, sodium hydroxide, potassium hydroxide, and cesium hydroxide), strong bases (such as lithium hydride, sodium hydride, t-butoxylithium, t-butoxysodium, t-butoxypotassium, lithium diisopropylamide, n-butyllithium, s-butyllithium, t-butyllithium, lithium hexamethyl disilazide, sodium hexamethyl disilazide, and potassium hexamethyl disilazide), dehydrating condensing agent (such as hydrochloric acid, sulfuric acid, diphosphorus pentaoxide, aluminum (III) chloride, boron trifluoride diethyl ether complex, ethylaluminum dichloride, and diethylaluminum chloride). Of these examples, inorganic salts (such as sodium carbonate, potassium carbonate, sodium hydrogen carbonate, and potassium hydrogen carbonate) are preferable.

The reaction should preferably be carried out in a polar solvent for a homogeneous system in consideration of the fact that the 4,5-dihydroxy-1,3-benzenedisulfonate as the starting material represented by formula (11) and the 1,4-benzodioxanesulfonic acid compound as the desired product represented by formula (9) are highly polar compounds. It is desirable to use a single solvent or a mixed solvent that keeps a uniform solution without solid precipitation from the start of reaction to the end of reaction.

Examples of the solvent include water, methanol, ethanol, n-propanol, i-propanol, n-butanol, N,N,-dimethylformamide (DMF), N,N,-dimethylacetamide (DMAc), N-methylpyrrolidone (NMP), N,N-dimethylimidazolidinone (DMI), dimethylsulfoxide (DMSO), tetrahydrofuran (THF), and dioxane. Of these examples, water is referable. These solvents may be used in combination with one another.

In the case where the substrate for the reaction is an (o-dihydroxybenzene) sulfonate, it is desirable to use water alone or a mixed solvent of water and any of the above-mentioned organic solvents. The resulting solution gives a homogenous system for conversion into a dioxane derivative.

The reaction temperature usually ranges from −50° C. to the boiling point of the solvent used. It should preferably be 20 to 200° C., particularly 60 to 100° C. The reaction time is usually 0.1 to 100 hours.

After the reaction is complete, the solvent is distilled away and the reaction product is extracted with a solvent (such as methanol) and washed with an organic solvent. In this way there is obtained a 1,4-benzodioxanesulfonate.

The thus obtained 1,4-benzodioxanesulfonate is treated with a cation-exchange resin, so that there is obtained the desired 1,4-benzodioxanesulfonic acid compound represented by formula (9).

The 1,4-benzodioxanesulfonic acid compound represented by formula (9) may be treated with a crosslinking agent, which acts on the OH group (or the XH group in formula (10)), for conversion into oligomer or polymer.

Examples of the crosslinking agent include hydrocarbon compounds having two or more substituent groups, such as halogen atoms, hydroxyl groups, amino groups, aldehyde groups, carboxyl groups, ester groups, and alkoxyl groups. The one which has at least one aromatic ring is desirable from the standpoint of good heat resistance, good charge transporting performance, and good solubility in organic solvents.

Preferred examples of the crosslinking agent include benzaldehyde, benzoic acid, benzoic ester, 1-naphthoaldehyde, 2-naphthoaldehyde, 2,4,6-trimethoxy-1,3,5-triazine, bis(4-fluorophenyl)sulfone, bis(4-fluoro-3-nitrophenyl)sulfone, perfluorobiphenyl, 2,2-bis(4-glycidyloxyphenyl)propane, and poly(vinylbenzyl chloride).

The 1,4-benzodioxanesulfonic acid compound represented by formula (9) may be halogenated for conversion into a 1,4-benzodioxanesulfonic acid compound represented by formula (12)

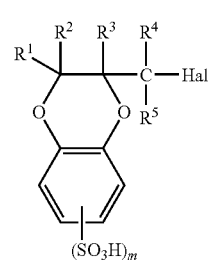

(12)

(where $R^1$ to $R^5$ and m are defined as above, and Hal denotes a halogen atom.) This compound may also be treated with a crosslinking agent.

Preferred examples of the crosslinking agent include (1,1'-biphenyl)-4,4'-diol, 4,4'-ethylidenebisphenol, 4,4'-cyclohexylidenebisphenol, 4,4'-cyclopentylidenebisphenol, 4,4'-(phenylmethylene)bisphenol, 4,4'-(1-phenylethylidene)bisphenol, 4,4'-methylenebisphenol, 4,4'-(2-methylpropylidene)bisphenol, 4,4'-methylenebis(2-fluorophenol), 4,4'-isopropylidenebis(2-fluorophenol), 4,4'-[(4-fluorophenyl)methylene]bis(2-fluorophenol), 4,4'-[2,2,2-trifluoro-1-(trifluoromethyl)ethylidene]bisphenol, 4,4'-(diphenylmethylene)bisphenol, 4,4'-dihydroxy-p-terphenyl, 4,4'-oxybisphenol, and 4,4'-(diphenylsilylene)bisphenol.

The method for crosslinking is not specifically restricted. The ordinary nucleophilic substitution reaction may be used.

In the case where the crosslinking agent having as many crosslinking sites as n is used to n-merize the compound represented by formula (9) or (10), the amount of the crosslinking agent should preferably be 1/n moles for the amount of the compound represented by formula (9) or (10).

Examples of the catalyst include strong bases (such as lithium hydride, sodium hydride, t-butoxylithium, t-butoxysodium, t-butoxypotassium, lithium-diisopropylamide, n-butyllithium, s-butyllithium, t-butyllithium, lithium hexamethyl disilazide, sodium hexamethyl disilazide, and potassium hexamethyl disilazide) and the dehydrating condensing agent (such as hydrochloric acid, sulfuric acid, diphosphorus pentaoxide, aluminum (III) chloride, boron trifluoride diethyl ether complex, ethylaluminum dichloride, and diethylaluminum chloride). They should preferably be used 1.0 to 1.5 times (in mole) as much as the amount of the compound represented by formula (9) or (10).

The solvent should preferably be aprotic polar organic ones, such as DMF, DMAc, NMP, DMI, DMSO, THF, and dioxane. Of these solvents, DMI and DMSO are desirable for dissolution of 1,4-benzodioxanesulfonic acid compound with low solubility.

The reaction temperature usually ranges from −50° C. to the boiling point of the solvent used. It should preferably be 0 to 140° C. The reaction time is usually 0.1 to 100 hours.

After the reaction is complete, the solvent is distilled away and the reaction product is treated with a cation exchange resin to protonize the sulfonate and extracted with a solvent (such as methanol) and finally reprecipitated for purification.

The 1,4-benzodioxanesulfonic acid compound represented by formula (1) according to the present invention may also be synthesized by another method, which involves ordinary sulfonation of 1,4-benzodioxane with conc. sulfuric acid, fuming sulfuric acid, and halosulfuric acid.

The thus obtained 1,4-benzodioxanesulfonic acid compound represented by formula (1) according to the present invention may also be crosslinked to give the 1,4-benzodioxanesulfonic acid compound represented by formula (2). Crosslinking may be accomplished with any of the following compounds. Resorcinol, fluoroglucinol, 2,2-bis(4-hydroxyphenyl)hexafluoropropane, octafluoro-4,4-biphenol, (1,1'-biphenyl)-4,4'-diol, 4,4'-ethylidenebisphenol, 4,4'-cyclohexylidenebisphenol, 4,4'-cyclopentylidenebisphenol, 4,4'-(phenylmethylene)bisphenol, 4,4'-(1-phenylethylidene)bisphenol, 4,4'-methylenebisphenol, 4,4'-(2-methylpropylidene)bisphenol, 4,4'-methylenebis(2-fluorophenol), 4,4'-isopropylidenebis(2-fluorophenol), 4,4'-[(4-fluorophenyl)methylene]bis(2-fluorophenol), 4,4'-[2,2,2-trifluoro-1-(trifluoromethyl)ethylidene]bisphenol, 4,4'-(diphenylmethylene)bisphenol, 4,4'-dihydroxy-p-terphenyl, 4,4'-oxybisphenol, and 4,4'-(diphenylsilylene)bisphenol.

The 1,4-benzodioxanesulfonic acid compound represented by formula (1) according to the present invention may be crosslinked with polymeric crosslinking groups for conversion into the 1,4-benzodioxanesulfonic acid compound represented by formula (2) or (3). To be concrete, it may be crosslinked with poly(4-hydroxystyrene) or novolak resin or the like.

The 1,4-benzodioxanesulfonic acid compound represented by any of formulas (1) to (4) may be used as an electron acceptor substance because it has the electron accepting properties.

The term "charge transporting varnish" as used in the present invention means a varnish (in solvent solution form) which contains at least a charge transporting substance essential for charge transportation and an electron acceptor substance represented by any of formulas (1) to (4). The electron acceptor substance improves the charge transporting performance and uniform film-forming ability. It is synonymous with the charge accepting dopant.

The charge transporting varnish according to the present invention may contain its constituents completely dissolved or uniformly dispersed in a solvent.

Also, charge transportation is synonymous with conduction, and it is synonymous with hole transportation in the present invention. The charge transporting varnish may be capable of charge transportation by itself or the solid film obtained from the varnish may be capable of charge transportation.

The charge transporting substance used in the present invention is not specifically restricted so long as it is a charge transporting oligomer or polymer which is soluble or uniformly dispersible in a solvent. An oligomer having one kind of continuous conjugated units is preferable, or an oligomer having a combination of different continuous conjugated units is preferable.

The conjugated unit is not specifically restricted so long as it is an atom, aromatic ring, or conjugated group capable of charge transportation. Preferred examples of the conjugated unit include a substituted or unsubstituted di- to tetravalent aniline group, thiophene group, furan group, pyrrole group, ethynilene group, vinylene group, phenylene group, naphthalene group, oxadiazole group, quinoline group, silol group, silicon atom, pyridine group, phenylenevinylene group, fluorene group, carbazole group, triarylamine group, metal-(or metalless)-phthalocyanine group, and metal-(or metalless)-porphyrin.

Examples of the substituent group include hydrogen, hydroxyl group, halogen group, amino group, silanol group, thiol group, carboxyl group, sulfonic acid group, phosphoric acid group, phosphate ester group, ester group, thioester group, amide group, nitro group, monovalent hydrocarbon group, organoxy group, organoamino group, organosilyl group, organothio group, acyl group, and sulfone group. These functional groups may be substituted with other functional groups.

Examples of the monovalent hydrocarbon group include alkyl groups (such as methyl group, ethyl group, n-propyl group, i-propyl group, n-butyl group, i-butyl group, t-butyl group, n-hexyl group, n-octyl group, 2-ethylhexyl group, and decyl group), cycloalkyl groups (such as cyclopentyl group and cyclohexyl group), bicycloalkyl groups (such as bicyclohexyl group), alkenyl groups (such as vinyl group, 1-propenyl group, 2-propenyl group, isopropenyl group, 1-methyl-2-propenyl group, 1-, 2-, or 3-butenyl group, and hexenyl group), aryl groups (such as phenyl group, xylyl group, tolyl group, diphenyl group, and naphthyl group), and aralkyl groups (such as benzyl group, phenylethyl group, and phenylcyclohexyl group). These monovalent hydrocarbon groups may have their hydrogen atoms replaced partly or entirely by halogen atoms, hydroxyl groups, or alkoxyl groups.

Examples of the organoxy group include alkoxyl groups, alkenyloxy groups, and aryloxy groups. The alkyl group, alkenyl group, and aryl group in them are the same one as enumerated above.

Examples of the organoamino group include alkylamino groups (such as methylamino group, ethylamino group, propylamino group, butyamino group, pentylamino group, hexylamino group, heptylamino group, octylamino group, nonylamino group, decylamino group, and laurylamino group), dialkylamino groups (such as dimethylamino group, diethylamino group, dipropylamino group, dibutylamino group, dipentylamino group, dihexylamino group, diheptylamino group, dioctylamino group, dinonylamino group, and didecylamino group), cycloalkylamino groups (such as cyclohexylamino group), and morpholino group.

Example of the organosilyl group include trimethylsilyl group, triethylsilyl group, tripropylsilyl group, tributylsilyl group, tripentylsiyylyl group, trihexylsilyl group, pentyldimethylsilyl group, hexyldimethylsilyl group, octyldimethylsilyl group, and decyldimethylsilyl group.

Examples of the organothio group include alkylthio groups (such as methylthio group, ethylthio group, propylthio group, butylthio group, pentylthio group, hexylthio group, heptylthio group, octylthio group, nonylthio group, decylthio group, and laurylthio group).

Examples of the acyl group include formyl group, acetyl group, propionyl group, butylyl group, isobutylyl group, varelyl group, isovarelyl group, and benzoyl group.

No specific restrictions are imposed on the number of carbon atoms in the above-mentioned monovalent hydrocarbon group, organoxy group, organoamino group, organosilyl group, organothio group, and acyl group. The carbon number is usually 1 to 20, preferably 1 to 8.

Preferred examples of the substituent group include fluorine, sulfonic acid group, substituted or unsubstituted organoxy group, alkyl group, and organosilyl group. The conjugated chain formed by connection of conjugated units may contain a cyclic moiety.

The charge transporting substance should preferably have a molecular weight no larger than 5000 from the standpoint of high solubility and no smaller than 200 from the standpoint of low volatility and charge transporting performance. It should be highly soluble in at least one solvent. It may have a number-average molecular weight of 5000 to 500000 so long as it is highly soluble in at least one solvent.

A preferred example of the charge transporting substance is the oligoaniline derivative disclosed in Japanese Patent Laid-open No. 2002-151272. It is represented by formula (13) below.

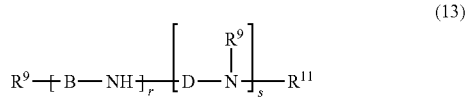

(13)

(where $R^9$ denotes a hydrogen atom, monovalent hydrocarbon group, or organoxy group; $R^{10}$ and $R^{11}$ each independently denotes a hydrogen atom or monovalent hydrocarbon group; B and D each independently denotes a divalent group represented by formula (14) or (15) below.

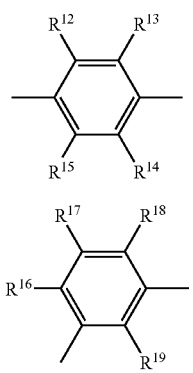

(14)

(15)

where $R^{12}$ to $R^{19}$ each independently denotes a hydrogen atom, hydroxyl group, monovalent hydrocarbon group, organoxy group, acyl group, or sulfone group; and r and s each independently denotes an integer of 1 or larger, satisfying r+s≦20.)

The monovalent hydrocarbon group, organoxy group, and acyl group represented by $R^9$ to $R^{16}$ are the same one as mentioned above.

The oligoaniline represented by formula (16) below (or quinonediimine derivative in its oxidized form) is preferable because it has a broader π conjugate system in the molecule and the resulting charge transporting thin film has improved charge transporting performance.

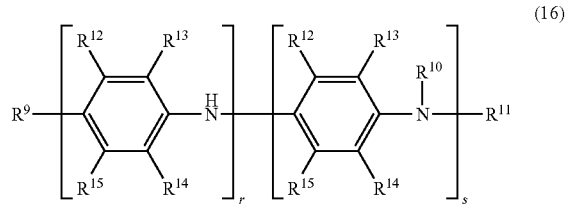

(16)

(where $R^9$ to $R^{16}$, r, and s are defined as above.)

Incidentally, identical symbols on the two benzene rings in formula (16) denote identical or different substituent groups.

In formulas (13) and (16), the sum of r+s should preferably be no smaller than 4 from the standpoint of good charge transporting performance and no larger than 16 from the standpoint of good solubility in solvents.

It is desirable that the oligoaniline derivative represented by formula (16) has its both ends capped with phenyl groups. In this case, $R^9$ is a hydrogen atom and $R^{11}$ is a phenyl group.

It is possible to use only one kind of or more than two kinds of the charge transporting substance.

Examples of the compound represented by formula (16) include oligoaniline derivatives soluble in organic solvents, such as phenyltetraaniline, phenylpentaaniline, tetraaniline (aniline tetramer), and octaaniline (aniline octamer).

The charge transporting substance may be synthesized in any other method without specific restrictions. The synthesis of oligoaniline described in the following documents may be used. Bulletin of Chemical Society of Japan, 1994, vol. 67, p. 1749 to 1752; and Synthetic Metals, U.S., 1997, vol. 84, p. 119 to 120. The synthesis of oligothiophene described in the following documents may also be used. Heterocycles, 1987, vol. 26, p. 939 to 942; and Heterocycles, 1987, vol. 26, p. 1793 to 1796. It is desirable that the oligoaniline derivative should undergo reduction with hydrazine.

The charge transporting varnish of the present invention may be dissolved in a mixed solvent containing 5 to 100 wt % of high-solvency solvent capable of dissolving the charge transporting substance and charge acceptor substance. The varnish should be dissolved completely or dispersed uniformly in the high-solvency solvent.

The high-solvency solvent is not specifically restricted. It includes, for example, water, methanol, N,N-dimethylformamide, N,N-dimethylacetamide, N-methylpyrrolidone, N,N'-dimethylimidazolidinone, dimethylsulfoxide, chloroform, toluene, and methanol.

The charge transporting varnish of the present invention should preferably have a viscosity of 10 to 200 mPa·s (particularly 50 to 150 mPa·s) at 20° C. and contain at least one kind of high-viscosity organic solvent having a boiling point of 50 to 300° C. (particularly 150 to 250° C.) under normal pressure.

The high-viscosity organic solvent is not specifically restricted. It includes, for example, cyclohexanol, ethyleneglycol, ethyleneglycol diglycidyl ether, 1,3-octyleneglycol, diethyleneglycol, dipropyleneglycol, triethyleneglycol, tripropyleneglycol, 1,3-butanediol, 1,4-butanediol, propylene glycol, and hexyleneglycol.

The charge transporting varnish of the present invention should preferably contain the high-viscosity organic solvent in an amount of 5 to 80 wt %, which is small enough to prevent precipitation of solids.

Incidentally, the charge transporting varnish of the present invention may also contain an additional solvent in an amount of 1 to 90 wt %, preferably 1 to 50 wt %, for the total amount of the solvents. The additional solvent is intended to improve the ability of the varnish to wet the substrate, to adjust the surface tension, polarity, and boiling point of the solvent, and to make the film flat at the time of baking.

Examples of such an additional solvent include butylcellosolve, diethyleneglycol diethyl ether, dipropyleneglycol monomethyl ether, ethylcarbitol, diacetonealcohol, γ-butylolactone, and ethyl lactate.

The above-mentioned charge transporting varnish is applied to a substrate, followed by solvent evaporation, to form a charge transporting film on a substrate.

The method for varnish application is not specifically restricted. It includes dipping, spin coating, transfer printing, roll coating, and brushing, which are capable of uniform film forming.

The method for solvent evaporation is not specifically restricted. It includes evaporation with the help of hot plate or oven under an adequate atmosphere, such as air, nitrogen (inert gas), or vacuum. Evaporation in this way gives a uniform film.

The baking temperature is not specifically restricted so long as it is high enough to evaporate solvents. It should preferably be 40 to 250° C. Baking may be accomplished in two or more stages at different temperatures so as to form a uniform film or to cause reaction to proceed on the substrate.

The charge transporting thin film formed by varnish application and ensuing solvent evaporation may have any thickness which is not specifically restricted. The thickness should preferably be 5 to 200 nm if the thin film is used as the charge injection layer in an organic EL device. The film thickness may be adjusted by varying the concentration of solids in the varnish or by varying the amount of the varnish to be applied to the substrate.

The following method and materials are used to produce the OLED device with the charge transporting varnish of the present invention. They are merely exemplary.

The first step is to clean the electrode substrate with a detergent and a liquid (such as alcohol or pure water). The anode substrate should preferably undergo surface treatment (such as ozone treatment and oxygen-plasma treatment) right before the use, although such surface treatment is not necessary if the anode material is composed mainly of organic matter.

The hole transporting varnish may be used for the OLED device in the following manner. First, the hole transporting varnish is applied to the anode substrate to form a hole transporting thin film thereon by the film forming method mentioned above. The substrate is placed in a vacuum deposition apparatus. On the substrate are sequentially formed by vapor deposition a hole transporting layer, an emitting layer, an electron transporting layer, and an electron injection layer, and a cathode metal layer. Thus there is obtained the desired OLED device. A carrier blocking layer may be interposed between any two adjacent layers to control the emitting region.

The anode may be formed from a transparent electrode material such as indium tin oxide (ITO) and indium zinc oxide (IZO). The anode should preferably undergo planarizing process. It is also possible to form the anode from a polythiophene derivative or polyaniline which is capable of charge transportation.

The hole transporting layer may be formed from any of the following materials. Triarylamines, such as (triphenylamine)dimer derivative (TPD), (α-naphthyldiphenylamine)dimer (α-NPD), and [(triphenylamine)dimer]spirodimer (Spiro-TAD); starburst amines, such as 4,4',4"-tris[3-methylphenyl(phenyl)amino]triphenylamine (m-MTDATA), and 4,4',4"-tris[1-naphthyl(phenyl)amino]triphenylamine (1-TNATA); and oligothiphenes, such as 5,5"-bis-{4-[bis(4-methylphenyl)amino]phenyl}-2,2':5',2"-terthiophene (BMA-3T).

The emitting layer may be formed from any of the following materials. Tris(8-quinolinolato)aluminum (III) ($Alq_3$), bis(8-quinolinolato)zinc (II) ($Znq_2$), bis(2-methyl-8-quinolinolato)(p-phenylphenolate)aluminum (III) (BAlq), and 4,4'-bis(2,2-diphenylvinyl)biphenyl (DPVBi). Incidentally, the emitting layer may also be formed by codeposition from an electron transporting material (or hole transporting material) and an emitting dopant.

Examples of the electron transporting material include $Alq_3$, BAlq, DPVBi, (2-(4-biphenyl)-5-(4-t-butylphenyl)-1,3,4-oxadiazole) (PBD), triazole derivative (TAZ), bathocuproine (BCP), and silol derivative.

Examples of the emitting dopant include quinacridone, rubrene, coumarin 540, 4-(dicyanomethylene)-2-methyl-6-(p-dimethylaminostyryl)-4H-pyran (DCM), tris(2-phenylpyridine)iridium (III) ($Ir(ppy)_3$), and (1,10-phenanthroline)-tris (4,4,4-trifluoro-1-(2-thieny)-butane-1,3-dionate) europium (III) ($Eu(TTA)_3phen$).

The carrier blocking layer may be formed from any of PBD, TAZ, and BCP.

The electron injection layer may be formed from any of lithium oxide ($Li_2O$), magnesium oxide (MgO), alumina ($Al_2O_3$), lithium fluoride (LiF), magnesium fluoride ($MgF_2$), strontium fluoride ($SrF_2$), lithium quinolinenolide (Liq), lithium acetylacetonate complex (Li(acac)), lithium acetate, and lithium benzoate.

The material for the cathode includes aluminum, magnesium-silver alloy, aluminum-lithium alloy, lithium, sodium, potassium, and cesium.

The charge transporting varnish of the present invention may be used for the OLED device in the following manner.

First, the electron transporting varnish is applied to a cathode substrate, so that an electron transporting thin film is formed on the cathode substrate. The coated substrate is placed in a vacuum deposition apparatus. On the substrate are sequentially formed an electron transporting layer, an emitting layer, a hole transmitting layer, and a hole injection layer from the same materials as mentioned above. Finally, the anode is formed by sputtering. Thus there is obtained the desired OLED device.

The charge transporting varnish of the present invention may be used to produce the PLED device in any manner without specific restrictions. A typical method is given below.

The steps of vacuum deposition for the hole transporting layer, emitting layer, electron transporting layer, and electron injection layer in the OLED device mentioned above are replaced by a single step of forming an emitting charge transporting polymeric layer. In this way there is obtained the PLED device having a charge transporting thin film formed from the charge transporting varnish of the present invention.

To be concrete, the process consists of applying the hole transporting varnish to the anode substrate in the same way as mentioned above, thereby forming a hole transporting thin film on the electrode, forming thereon an emitting charge transporting polymeric layer, and finally forming the cathode by vapor deposition. Thus there is obtained the desired PLED device.

An alternative process consists of applying the electron transporting varnish to the cathode substrate, thereby forming an electron transporting thin film on the electrode by the same way as mentioned above, forming thereon an emitting charge transporting polymeric layer, and finally forming the anode by sputtering, vapor deposition, or spin coating. Thus there is obtained the desired PLED device.

The cathode and anode may be formed from the same materials as enumerated above for the OLED device. They should undergo cleaning and surface treatment in the same way as mentioned above.

The emitting charge transporting polymeric layer may be formed in the following way. First, an emitting charge transporting polymeric material alone or in combination with an emitting dopant is dissolved or dispersed uniformly in a solvent. The resulting solution or dispersion is applied to an electrode substrate on which the hole injection layer has been formed. Finally, the solvent is distilled away.

The material for the emitting charge transporting polymeric layer includes, for example, polyfluorene derivative such as poly(9,9-dialkylfluorene) (PDAF), polyphenylenevinylene derivative such as poly(2-methoxy-5-(2'-ethylhexoxy)-1,4-phenylenevinylene) (MEH-PPV), polythiophene derivative such as poly(3-alkylthiophene) (PAT), and polyvinylcarbazole (PVCz).

The solvent includes, for example, toluene, xylene, and chloroform. Dissolution or dispersion may be accomplished by stirring, stirring with heating, or ultrasonic dispersion.

The method for coating is not specifically restricted; it includes, for example, dipping, spin coating, transfer printing, roll coating, and brushing. Coating should preferably be carried out in an atmosphere of inert gas such as nitrogen and argon.

Solvent evaporation may be accomplished by heating in an inert gas or vacuum with the help of oven or hot plate.

EXAMPLE

The invention will be described in more detail with reference to the following Synthetic Example, Examples and Comparative Examples, which are not intended to restrict the scope thereof.

Example 1

There was synthesized 2-hydroxymethyl-1,4-benzodioxanedisulfonic acid (HMBDDS for short hereinafter) according to the following reaction formula (17).

In a reaction vessel was placed 25.40 g of Tiron(4,5-dihydroxy-1,3-benzenedisulfonic acid disodium salt monohydrate, from Kanto Chemical Co., Inc.). To the reaction vessel was sequentially added 9.723 g of anhydrous sodium carbonate and 508 ml of pure water. The reactants were dissolved by stirring at room temperature for 10 minutes. To the reaction vessel was added 7.19 ml of epichlorohydrin. The reactants were stirred at room temperature for 2 hours and then at 70° C. for 13 hours. The reaction solution was allowed to cool to room temperature and then concentrated to dryness under reduced pressure. The residues were crushed with 630 ml of methanol and remaining solids were filtered off and washed with methanol. Washings were added to the filtrate. The filtrate was concentrated to dryness under reduced pressure. The residues were dissolved in 500 ml of water. The solution was extracted with 200 ml of ethyl acetate. The water layer was washed twice with 200 ml each of ethyl acetate. The water layer was concentrated to dryness under reduced pressure. The residues were thoroughly crushed with 420 ml of water, and remaining solids were filtered off. The filtrate was concentrated to dryness under reduced pressure. Thus there was obtained 20.058 g of white powder. (Yield: 73%)

The thus obtained white powder was analyzed by $^1$H-NMR, $^{12}$C-NMR, and ESI-MS. An NMR spectrum ascribed to HMBDDS was obtained, and m/z 325 was detected.

$^1$H-NMR (400 MHz, D$_2$): δ 3.57 (2H, dd), 3.66 (2H, dd), 3.79 (1H, dddd), 7.53 (1H, d), 7.79 (1H, d)

$^{13}$C-NMR (100 MHz, D$_2$O): δ 60.3, 62.6, 64.9, 72.2, 73.7, 74.9 MS (ESI−): m/z 325 (M-H)$^-$

The white powder of HMBDDS disodium salt (616 mg) was protonized with the help of cation exchange resin Dowex 650C (H-type, from Muromachi Chemicals Inc.). Thus there was obtained 475 mg of HMBDDS (in a colorless oily form). The yield was 87% at the time of ion exchange operation.

Example 2

There was synthesized an oligomer 1 of 1,4-benzodioxane compound represented by formula (18) and then there was synthesized an oligomer 1 of 1,4-benzodioxanesulfonic acid compound represented by formula (19) in the following manner. The two oligomers are abbreviated as BDO-1 and BDSO-1, respectively, hereinafter.

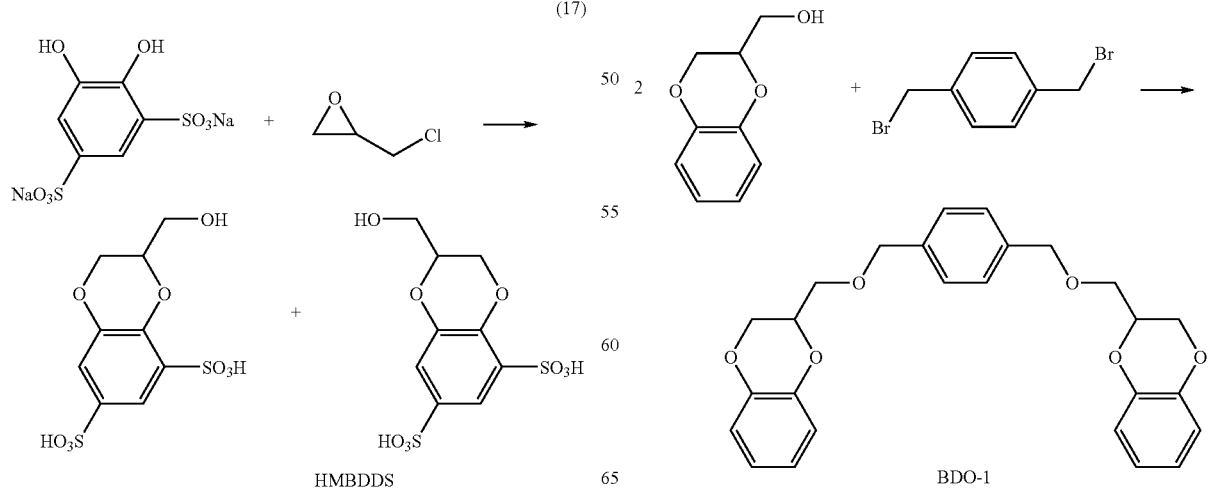

In a reaction vessel was placed 15.07 g of 2-hydroxymethyl-1,4-benzodioxane. To the reaction vessel was added 300 ml of dehydrated DMF for dissolution under an atmosphere of nitrogen. To the reaction vessel was further added 4.276 g of 60% sodium hydride. The reactants were stirred at room temperature for 70 minutes and then at 40° C. for 70 minutes under an atmosphere of nitrogen. The reaction solution was allowed to cool to room temperature. To the reaction solution was added 9.974 g of p-xylenedibromide and then stirred at room temperature for 18 hours under an atmosphere of nitrogen. The reaction was suspended by adding 70 ml of saturated aqueous solution of ammonium chloride. The solution was concentrated to dryness under reduced pressure. To the residues was added 600 ml of ethyl acetate. The solution was washed three times with 150 ml of pure water. The organic layer was dried with anhydrous sodium sulfate and then concentrated to dryness under reduced pressure. The residue was recrystallized from ethyl acetate-hexane (5:6) mixed solvent. Thus there was obtained BDO-1 in the form of white crystal. (Yield: 8.62 g, 52%)

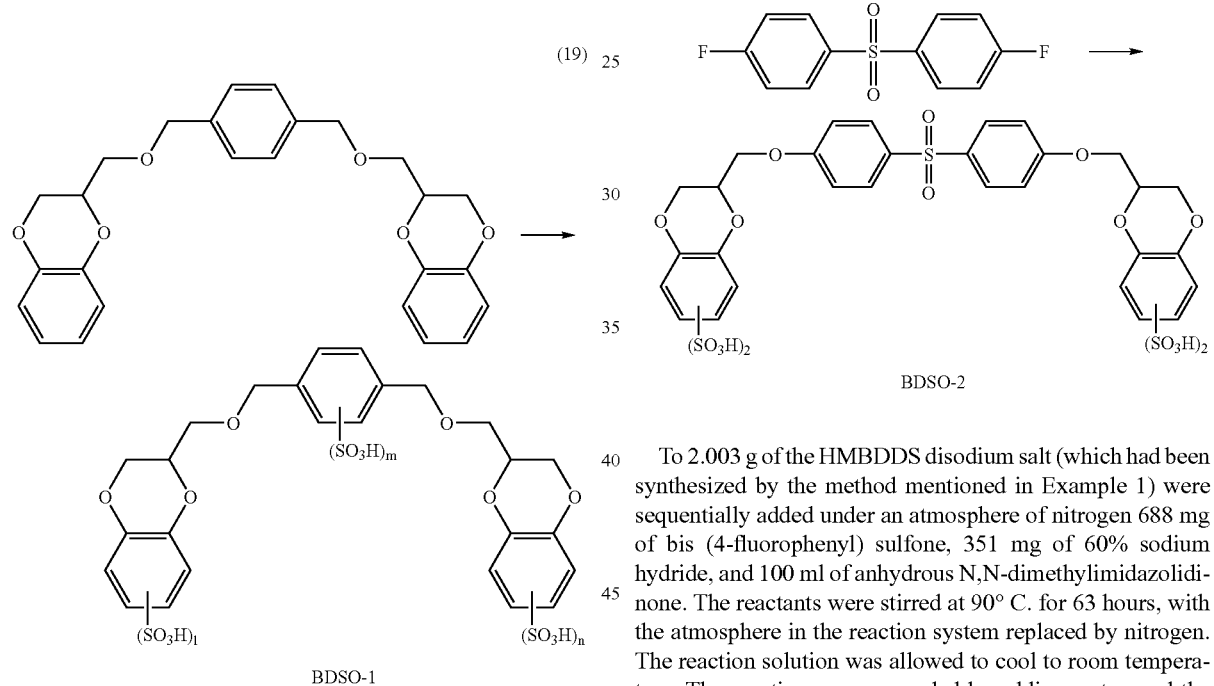

BDSO-1

Then, 8.62 g of BDO-1 was added with stirring over 40 minutes to 106 g of 30% fuming sulfuric acid cooled to 0° C. The reaction solution was stirred at 0° C. for 30 minutes and then at room temperature for 4 hours. The reaction solution was slowly added to 150 ml of methanol. To the methanol solution were added 750 ml of diethyl ether and 200 ml of methanol. After stirring at room temperature for 2 hours, precipitates were filtered off and dissolved in 80 ml of methanol. To the methanol solution was slowly added 500 ml of diethyl ether for reprecipitation by stirring at room temperature for 1 hour. Precipitates were filtered off. The same procedure for reprecipitation was repeated once again. The resulting solids were dried under reduced pressure. The dried solids were purified by column chromatography with Dowex 650C (H-type). Thus there was obtained BDSO-1 in the form of brown powder. (Yield: 5.83 g, 35%)

The result of elemental analysis indicates that BDSO-1 is composed of carbon (39.5%), hydrogen (4.4%), and sulfur (13%). The number of sulfonic acid groups (1+m+n) is estimated to be 2 to 4.

Example 3

There was synthesized an oligomer 2 of 1,4-benzodioxane-sulfonic acid compound according to the reaction formula (20) below. The oligomer is abbreviated as BDSO-2 hereinafter.

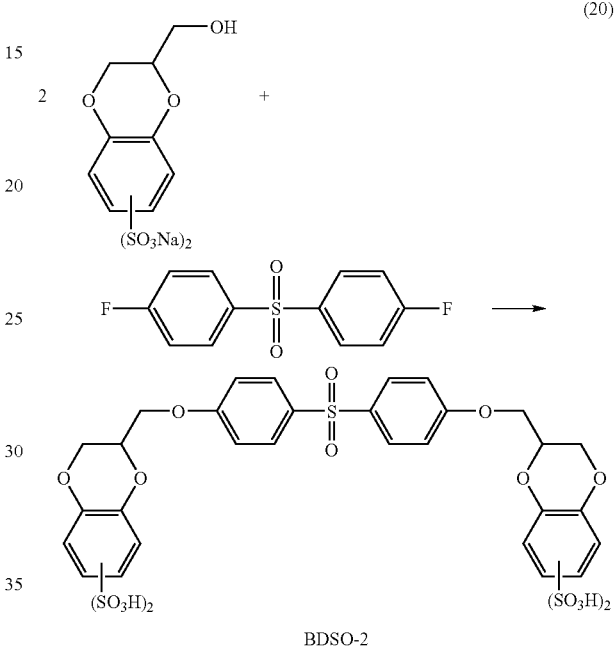

BDSO-2

To 2.003 g of the HMBDDS disodium salt (which had been synthesized by the method mentioned in Example 1) were sequentially added under an atmosphere of nitrogen 688 mg of bis (4-fluorophenyl) sulfone, 351 mg of 60% sodium hydride, and 100 ml of anhydrous N,N-dimethylimidazolidinone. The reactants were stirred at 90° C. for 63 hours, with the atmosphere in the reaction system replaced by nitrogen. The reaction solution was allowed to cool to room temperature. The reaction was suspended by adding water, and the reaction solution was concentrated to dryness under reduced pressure. To the residues were sequentially added 50 ml of pure water and about 10 g of cation exchange resin Dowex 650C (H-type). After filtration, the filtrate was concentrated to dryness under reduced pressure. To the residue was added 5 ml of methanol, and the solids which had separated out were filtered off. The filtrate was concentrated under reduced pressure. To the concentrated solution was added 2.5 ml of methanol, and the resulting solution was added to 100 ml of diethyl ether with stirring. After stirring at room temperature for 6 hours, the supernatant liquid was removed. The residue was purified by column chromatography with cation exchange resin Dowex 650C (H-type). Thus there was obtained 1.939 g of brown powder. (Yield: 83%)

This brown powder was analyzed by ESI-MS. A main peak (m/z 883) ascribed to BDSO-2 was detected MS (ESI–): m/z 883 (M+OH)⁻.

Example 4

There was synthesized an oligomer 3 of 1,4-benzodioxane-sulfonic acid compound according to the reaction formula (21) below. The oligomer is abbreviated as BDSO-3 hereinafter.

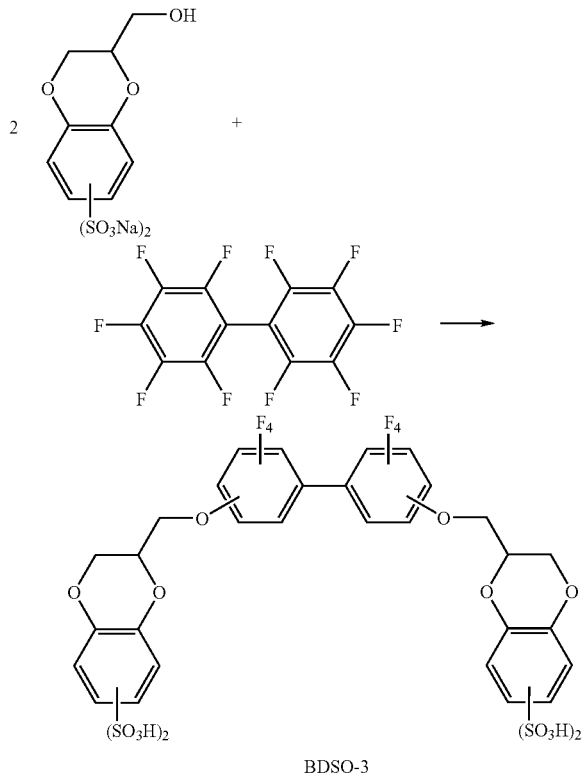

BDSO-3

To 1.999 g of the HMBDDS disodium salt (which had been synthesized by the method mentioned in Example 1) were sequentially added under an atmosphere of nitrogen 902 mg of perfluorobiphenyl, 348 mg of 60% sodium hydride, and 100 ml of anhydrous N,N-dimethylimidazolidinone. The reactants were stirred at 90° C. for 63 hours, with the atmosphere in the reaction system replaced by nitrogen. The reaction solution was allowed to cool to room temperature. The reaction was finished by adding water, and the reaction solution was concentrated to dryness under reduced pressure. To the residues were sequentially added 50 ml of pure water and about 10 g of cation exchange resin Dowex 650C (H-type). After filtration, the filtrate was concentrated to dryness under reduced pressure. To the residue was added 5 ml of methanol, and the solids which had separated out were filtered off. The filtrate was concentrated under reduced pressure. To the concentrated solution was added 2.5 ml of methanol, and the resulting solution was added to 100 ml of diethyl ether with stirring. After stirring at room temperature for 6 hours, the supernatant liquid was removed. The residue was purified by column chromatography with cation exchange resin Dowex 650C (H-type). Thus there was obtained 1.815 g of yellowish powder. (Yield: 71%)

This yellowish powder was analyzed by ESI-MS and MALDI-TOF-MS. A main peak ascribed to BDSO-3 was detected.

MS (ESI−): m/z 963 (M+OH)⁻ MS (ESI+): m/z 964 (M+NH₄)⁺ MS (MALDI-TOF-MS−): m/z 945 (M-H)⁻

Example 5

There was synthesized an oligomer 4 of 1,4-benzodioxane-sulfonic acid compound according to the reaction formula (22) below. The oligomer is abbreviated as BDSO-4 hereinafter.

(22)

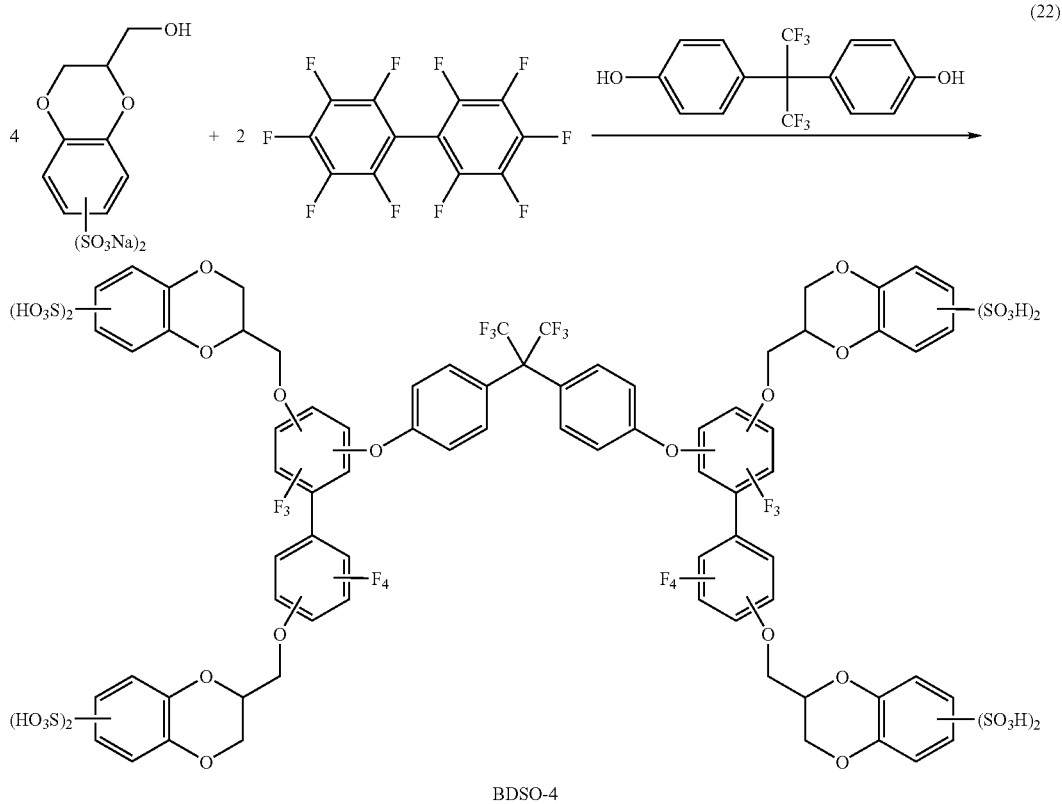

BDSO-4

To 0.993 g of the HMBDDS disodium salt (which had been synthesized by the method mentioned in Example 1) were sequentially added under an atmosphere of nitrogen 450 mg of perfluorobiphenyl, 160 mg of 60% sodium hydride, and 50 mL of anhydrous N,N-dimethylimidazolidinone. The reactants were stirred at 80° C. for 40 hours, with the atmosphere in the reaction system replaced by nitrogen. To the reaction system (kept at 80° C.) were added 56 mg of 60% sodium hydride and 227 mg of 2,2'-bis(4-hydroxyphenyl)hexafluoropropane. Stirring was continued at 80° C. for 33 hours. The reaction solution was allowed to cool to room temperature. The reaction was finished by adding 0.36 ml of water, and the reaction solution was concentrated to dryness under reduced pressure at a bath temperature of 50 to 75° C. To the residues was added 5 ml of methanol to make a uniform suspension. The suspension was added dropwise to 100 ml of diethyl ether with stirring. Stirring was continued at room temperature for 1 hour. Precipitates were collected by filtering by suction. The collected precipitates were washed with diethyl ether. To the washed precipitates was added 25 ml of methanol to make a uniform suspension. The suspension was filtered by suction. The filtrate was concentrated under reduced pressure. The concentrated filtrate was passed through about 40 ml of cation exchange resin Dowex 650C (H-type) which had been washed immediately before use. The distilled solvent was 50% aqueous solution of methanol. The distilled solvent was distilled away to give crude BDSO-4. To the crude BDSO-4 was added 3 ml of isopropanol, and the resulting solution was added dropwise to 60 ml of diethyl ether. After stirring at room temperature for 1 hour, the supernatant liquid was removed. The residue was dried under reduced pressure. Thus there was obtained 511 mg of yellowish powder. (Yield: 35%) This yellowish powder was analyzed by MALDI-TOF-MS. A peak ascribed to BDSO-4 was detected.

MS (MALDI-TOF-MS−): m/z 2187 (M-H)−

Example 6

There was synthesized an oligomer 5 of 1,4-benzodioxane-sulfonic acid compound according to the reaction formula (23) below. The oligomer is abbreviated as BDSO-5 hereinafter.

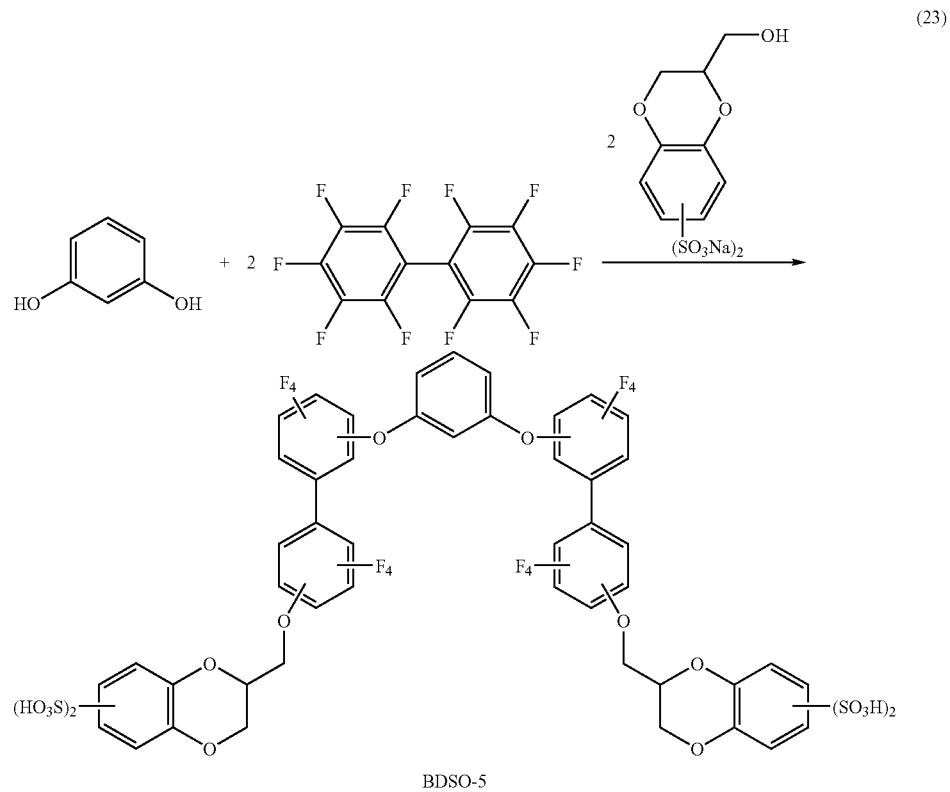

In 50 ml of anhydrous DMI were dissolved 904 mg of perfluorobiphenyl, 150 mg of resorcinol (from Kanto Chemical), and 166 mg of 60% sodium hydride under an atmosphere of nitrogen. The reactants were stirred at room temperature for 20 minutes and then at 80° C. for 7 hours. To the reaction system (kept at 80° C.) were sequentially added 163 mg of 60% sodium hydride and 1.003 g of the HMBDDS disodium salt (synthesized by the method mentioned in Example 1). The reactants were stirred at 80° C. for 39 hours. The reaction solution was allowed to cool to room temperature. Reaction was suspended by adding 0.36 ml of water. The reaction solution was concentrated to dryness under reduced pressure at a bath temperature of 50 to 75° C.

To the residues was added 5 ml of methanol to make a uniform suspension. The suspension was added dropwise to 100 ml of diethyl ether with stirring. Stirring was continued at room temperature for 1 hour. Precipitates were collected by filtering by suction. The collected precipitates were washed with diethyl ether. To the washed precipitates was added 25 ml of methanol to make a uniform suspension. The suspension was filtered by suction. The filtrate was concentrated under reduced pressure. The concentrated filtrate was passed through about 40 ml of cation exchange resin Dowex 650C (H-type) which had been washed immediately before use. The distilled solvent was 50% aqueous solution of methanol. The distilled solvent was distilled away to give crude BDSO-5. To the crude BDSO-5 was added 2.5 ml of isopropanol, and the resulting solution was added dropwise to 50 ml of diethyl ether. After stirring at room temperature for 1 hour, the supernatant liquid was removed. The residue was dried under reduced pressure. Thus there was obtained 1.023 g of light yellowish powder composed mainly of BDSO-5. (Yield: 56%)

This light yellowish powder was analyzed by MALDI-TOF-MS. A main peak ascribed to BDSO-5 was detected.

MS (MALDI-TOF-MS−): m/z 1349 (M−H⁻)

Example 7

There was synthesized an oligomer 6 of 1,4-benzodioxane-sulfonic acid compound according to the reaction formula (24) below. The oligomer is abbreviated as BDSO-6 hereinafter.

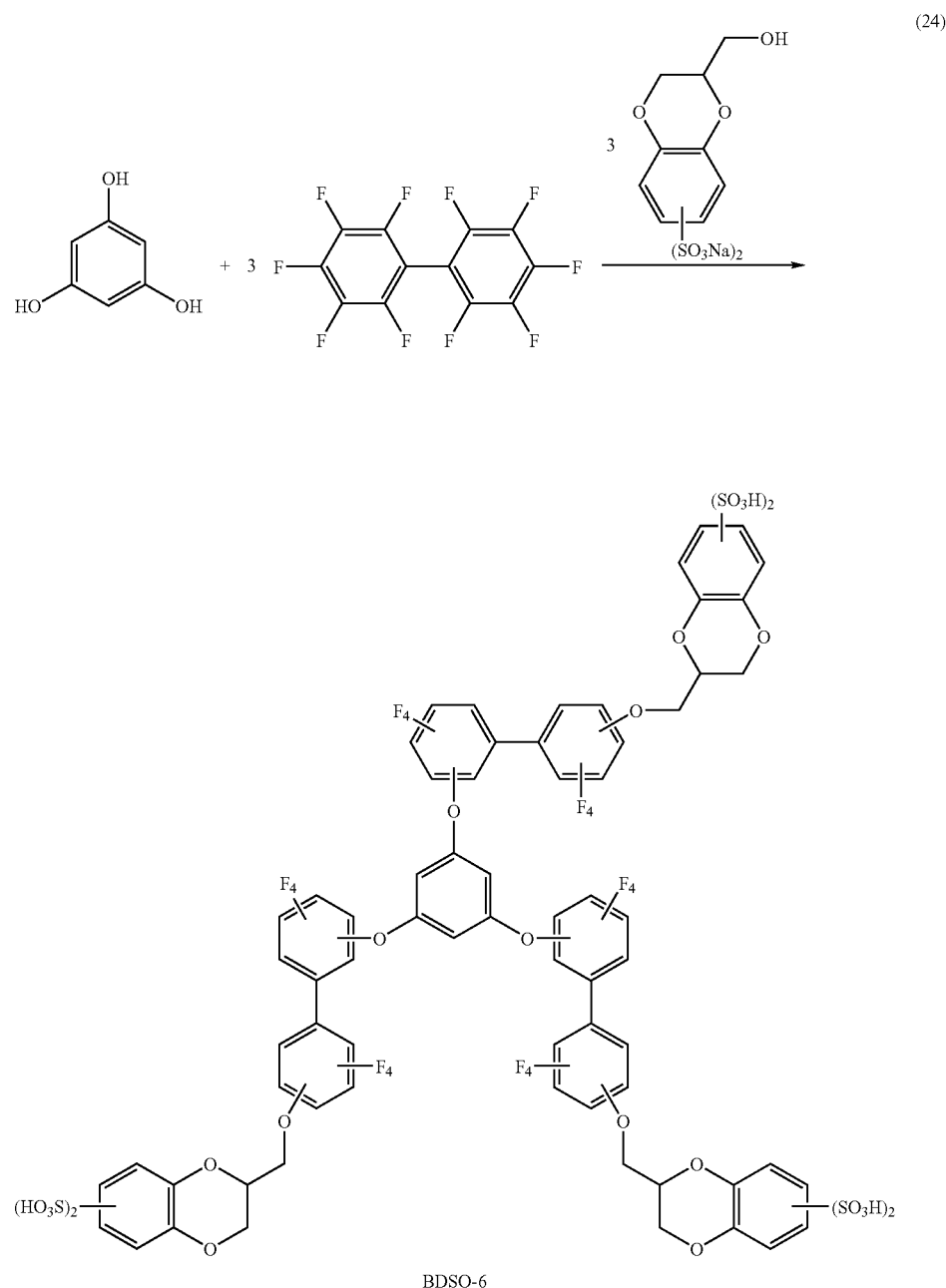

In 50 ml of anhydrous DMI were dissolved 903 mg of perfluorobiphenyl, 116 mg of phloroglucinol (from Kanto Chemical), and 164 mg of 60% sodium hydride under an atmosphere of nitrogen. The reactants were stirred at room temperature for 20 minutes, at 80° C. for 7 hours, at 100° C. for 3 hours, at 120° C. for 12 hours, and at 140° C. for 5 hours. To the reaction system (cooled to 80° C.) were sequentially added 166 mg of 60% sodium hydride and 1.029 g of the HMBDDS disodium salt (synthesized by the method mentioned in Example 1). The reactants were stirred at 80° C. for 71 hours.

The reaction solution was allowed to cool to room temperature. Reaction was finished by adding 0.36 ml of water. The reaction solution was concentrated to dryness under reduced pressure at a bath temperature of 50 to 75° C. To the residues was added 5 ml of methanol to make a uniform suspension. The suspension was added dropwise to 100 ml of diethyl ether with stirring. Stirring was continued at room temperature for 1 hour. Precipitates were collected by filtering by suction. The collected precipitates were washed with diethyl ether. To the washed precipitates was added 25 ml of methanol to make a uniform suspension. The suspension was filtered by suction. The filtrate was concentrated under reduced pressure. The concentrated filtrate was passed through about 40 ml of cation exchange resin Dowex 650C (H-type) which had been washed immediately before use. The distilled solvent was 10% aqueous solution of methanol.

The distilled solvent was distilled away to give crude BDSO-6. To the crude BDSO-5 was added 2 ml of isopropanol, and the resulting solution was added dropwise to 50 ml of diethyl ether. After stirring at room temperature for 1 hour, the supernatant liquid was removed. The residue was dried under reduced pressure. Thus there was obtained 1.362 g of yellowish brown powder containing BDSO-6. (Yield: 75%)

This yellowish brown powder was analyzed by MALDI-TOF-MS. A peak ascribed to BDSO-6 was detected.

MS (MALDI-TOF-MS−): m/z 1987 (M-H)−

Example 8

There was synthesized a polymer 1 of 1,4-benzodioxane-sulfonic acid compound according to the reaction formula (25) below. The polymer is abbreviated as BDSP-1 hereinafter.

(25)

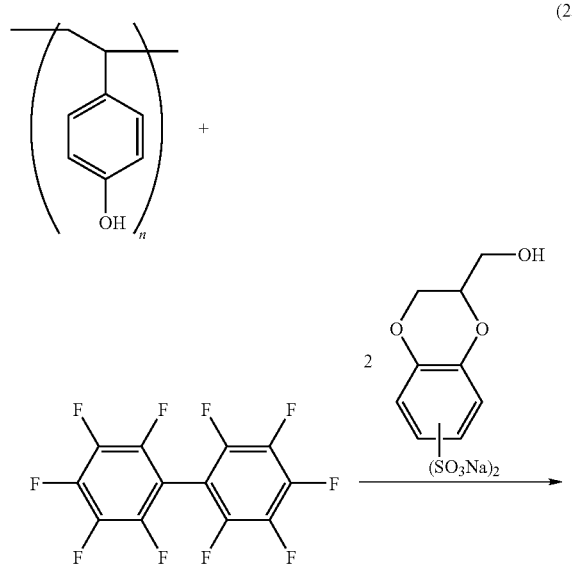

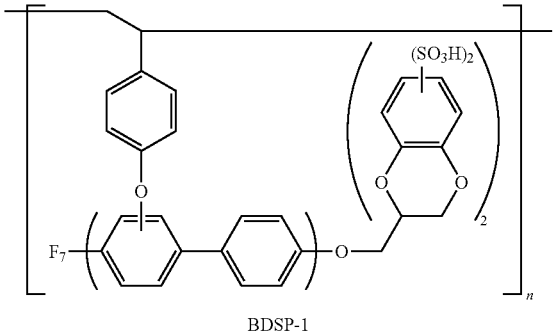

BDSP-1

In 20 ml of anhydrous NMP were dissolved 1.042 g of perfluorobiphenyl and 126 mg of 60% sodium hydride under an atmosphere of nitrogen. The reactants were heated to 80° C. while stirring. To the resulting suspension was added dropwise a PHS-NMP solution over 13 minutes, followed by stirring at 80° C. for 23 hours. The PHS—NMP was prepared by dissolving 254 mg of polyhydroxystyrene (having a number-average molecular weight of 2500, PHS for short) in 12.5 ml of anhydrous NMP at 80° C.

The reaction solution was allowed to cool to room temperature and then washed four times with 10 ml of hexane. The washed solution was concentrated to dryness under reduced pressure at a bath temperature of 50° C. To the residue were added 1.547 g of the HMBDDS disodium salt (synthesized by the method mentioned in Example 1), 102 mg of 60% sodium hydride, and 70 ml of dehydrated DMI under an atmosphere of nitrogen, followed by stirring at room temperature for 10 minutes. Stirring was continued at 80° C. (at a bath temperature of 82° C.) for 63 hours. The reaction solution was allowed to cool to room temperature. Reaction was finished by adding 0.37 ml of water. The reaction solution was concentrated to dryness under reduced pressure at a bath temperature of 50 to 75° C.

To the residue was added 5 ml of methanol to make a uniform suspension. The resulting suspension was added dropwise to 100 ml of diethyl ether with stirring. Stirring was continued at room temperature for 1 hour. Precipitates were collected by filtering by suction. The collected precipitates were washed with diethyl ether, and 45 ml of methanol was added to the washed precipitates to make a uniform suspension. Solids were filtered off by suction, and the resulting filtrate was concentrated under reduced pressure. The concentrated filtrate was passed through about 40 ml of cation exchange resin Dowex 650C (H-type) which had been washed immediately before use. The distilled solvent was 50% aqueous solution of methanol.

The distilled solvent was distilled away to give crude BDSP-1. To the crude BDSP-1 was added 2 ml of isopropanol, and the resulting solution was added dropwise to 50 ml of diethyl ether. After stirring at room temperature for 1 hour, the supernatant liquid was removed. The residue was dried under reduced pressure. Thus there was obtained 1.093 g of orange brown solid containing BDSP-1. (Yield: 50%)

Example 9

There was synthesized a polymer 2 of 1,4-benzodioxane-sulfonic acid compound according to the reaction formula (26) below. The polymer is abbreviated as BDSP-2 hereinafter.

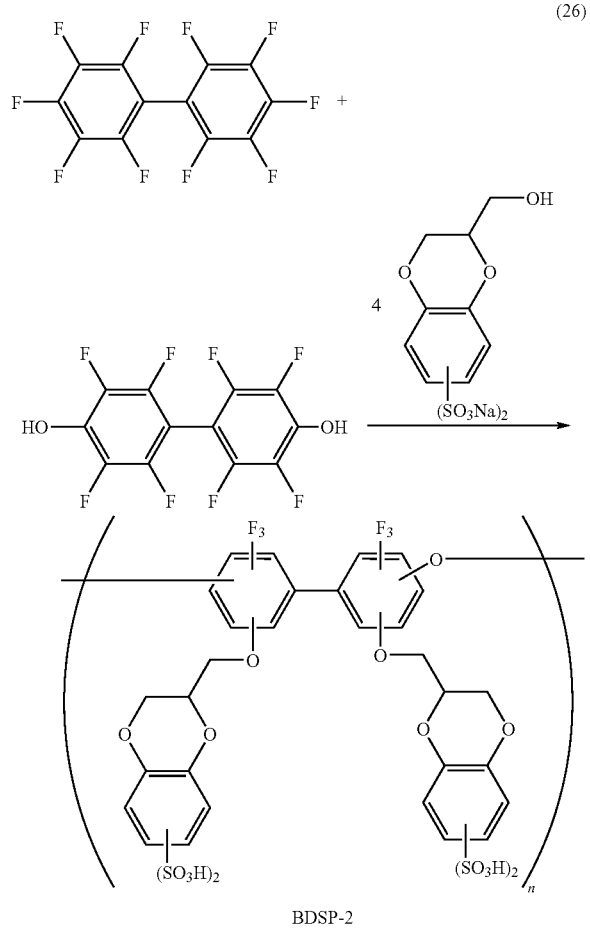

BDSP-2

In 50 ml of anhydrous DMI were dissolved 452 mg of perfluorobiphenyl, 446 mg of octafluoro-4,4'-biphenol (from Tokyo Kasei), and 84 mg of 60% sodium hydride under an atmosphere of nitrogen. The reactants were stirred at room temperature for 5 minutes, at 60° C. for 4 hours, and 80° C. for 24 hours. To the reaction system (kept at 80° C.) were added 1.012 g of the HMBDDS disodium salt (synthesized by the method mentioned in Example 1) and 163 mg of 60% sodium hydride, followed by stirring at 80° C. for 50 hours.

After cooling to room temperature, reaction was finished by adding 0.33 ml of water. The reaction solution was concentrated to dryness under reduced pressure at a bath temperature of 50 to 70° C. To the residue was added 4 ml of methanol to make a uniform suspension. The resulting suspension was added dropwise to 100 ml of diethyl ether with stirring. Stirring was continued at room temperature for 30 minutes. Precipitates were collected by filtering by suction. The collected precipitates were washed with diethyl ether, and 30 ml of methanol was added to the washed precipitates to make a uniform suspension. Solids were filtered off by suction, and the resulting filtrate was concentrated under reduced pressure. The concentrated filtrate was passed through about 40 ml of cation exchange resin Dowex 650C (H-type) which had been washed immediately before use. The distilled solvent was 17% aqueous solution of methanol.

The distilled solvent was distilled away to give crude BDSP-2. To the crude BDSP-2 was added 2.5 ml of isopropanol, and the resulting solution was added dropwise to 50 ml of diethyl ether. After stirring at room temperature for 1 hour, the supernatant liquid was removed. The residue was dried under reduced pressure. Thus there was obtained 864 mg of light yellowish powder containing BDSP-2. (Yield: 68%)

Synthesis Example 1

Synthesis of Phenyltetraaniline

A charge transporting varnish was prepared from the 1,4-benzodioxanesulfonic acid compound (obtained in any of Examples 1 to 9) as an electron acceptor substance and phenyltetraaniline (PTA for short hereinafter) represented by formula (27) below as a charge transporting substance.

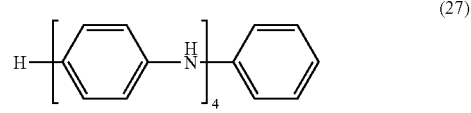

The method for synthesis of PTA is described first, and then the method for preparation of the varnish is illustrated in Examples 10 to 20.

Phenyltraaniline (PTA) was obtained as follows according to the method mentioned in Bulletin of Chemical Society of Japan, 1994, vol. 67, p. 1749 to 1752.

In 2 liters of toluene was dissolved 12.977 g of p-phenylenediamine. To the resulting solution was added 245.05 g of tetra-n-butoxytitanium as a dehydration-condensation agent. The reactants were heated at 70° C. for 30 minutes for dissolution. To the reaction system was added 53.346 g of p-hydroxydiphenylamine. Reaction was carried out at 100° C. for 24 hours under an atmosphere of nitrogen. After the reaction was complete, the reaction solution was filtered off and remaining solids were sequentially washed with toluene and ether and then dried. There were obtained silvery crystals. To the crystals were added 26 parts by weight of dioxane and 0.2 parts by weight of hydrazine monohydrate. With the atmosphere in the reaction system replaced by nitrogen, the crystals were dissolved by refluxing. To the resulting solution was added 25 parts by weight (based on the amount of the crystals) of toluene to make a suspension. After refluxing, 10 parts by weight of dioxane was added and refluxing was carried out for dissolution. The resulting solution was filtered off while hot.

The solids that had separated out from the filtrate were recrystallized. The resulting crystals were sequentially washed with (1:1) toluene-dioxane mixture and ether under an atmosphere of nitrogen. The washed crystals were dried at 60° C. for 10 hours under reduced pressure. The same procedure for recrystallization as above was repeated once again. Thus there was obtained 39.60 g of white crystals. (Yield: 75%)

Example 10

To a mixture of 95 mg of BDSO-1 (obtained in Example 2) and 50 mg of PTA (obtained in Synthesis Example 1) were sequentially added 1.90 ml of methanol and 1.87 ml of N,N-dimethylacetamide (DMAc for short hereinafter) for dissolution under an atmosphere of nitrogen. To the resulting solution was added 2.77 ml of cyclohexanol under an atmosphere of nitrogen with stirring at room temperature. Thus there was obtained a transparent brown varnish.

Example 11

To a mixture of 196 mg of BDSO-2 (obtained in Example 3) and 100 mg of PTA (obtained in Synthesis Example 1) was added 7.38 ml of DMF for dissolution under an atmosphere of nitrogen. Thus there was obtained a transparent yellowish varnish. This varnish gave no precipitates even after cooling to −25° C.

Example 12

To a mixture of 214 mg of BDSO-3 (obtained in Example 4) and 100 mg of PTA (obtained in Synthesis Example 1) was added 7.38 ml of DMF for dissolution under an atmosphere of nitrogen. Thus there was obtained a transparent light yellowish varnish. This varnish gave no precipitates even after cooling to −25° C.

Example 13

To a mixture of 107 mg of BDSO-3 (obtained in Example 4) and 100 mg of PTA (obtained in Synthesis Example 1) was added 7.38 ml of DMF for dissolution under an atmosphere of nitrogen. Thus there was obtained a transparent light yellowish varnish. This varnish gave no precipitates even after cooling to −25° C.

Example 14

To a mixture of 50.1 mg of BDSO-3 (obtained in Example 4) and 23.7 mg of PTA (obtained in Synthesis Example 1) was added 0.40 ml of DMAc for dissolution under an atmosphere of nitrogen. To the resulting solution (heated to 70° C.) were sequentially added 1.19 ml of cyclohexanol and 0.11 ml of ethylene glycol. After stirring and cooling to room temperature, there was obtained a transparent dark green varnish.

Example 15

To a mixture of 214 mg of BDSO-3 (obtained in Example 4) and 100 mg of PTA (obtained in Synthesis Example 1) were sequentially added 3.40 ml of DMF and 0.97 ml of ethyleneglycol for dissolution under an atmosphere of nitrogen. To the resulting solution was added dropwise 10.21 ml of cyclohexanol (heated to 50° C.). After stirring and cooling to room temperature, there was obtained a transparent dark green varnish. This varnish gave no precipitates even after cooling to −25° C.

Example 16

To a mixture of 107 mg of BDSO-3 (obtained in Example 4) and 100 mg of PTA (obtained in Synthesis Example 1) were sequentially added 3.40 ml of DMF and 0.97 ml of ethyleneglycol for dissolution under an atmosphere of nitrogen. To the resulting solution was added dropwise 10.21 ml of cyclohexanol (heated to 50° C.). After stirring and cooling to room temperature, there was obtained a transparent dark green varnish. This varnish gave no precipitates even after cooling to −25° C.

Example 17

To a mixture of 124 mg of BDSO-4 (obtained in Example 5) and 51 mg of PTA (obtained in Synthesis Example 1) were sequentially added 1.70 ml of DMF and 0.49 ml of ethyleneglycol for dissolution under an atmosphere of nitrogen. To the resulting solution was added dropwise 5.11 ml of cyclohexanol (heated to 50° C.). After stirring and cooling to room temperature, there was obtained a transparent green varnish. This varnish gave no precipitates even after cooling to −25° C.

Example 18

To a mixture of 152 mg of BDSO-5 (obtained in Example 6) and 51 mg of PTA (obtained in Synthesis Example 1) were sequentially added 1.70 ml of DMF and 0.49 ml of ethyleneglycol for dissolution under an atmosphere of nitrogen. To the resulting solution was added dropwise 5.11 ml of cyclohexanol (heated to 50° C.). After stirring and cooling to room temperature, there was obtained a transparent green varnish. This varnish gave no precipitates even after cooling to −25° C.

Example 19

To a mixture of 150 mg of BDSO-6 (obtained in Example 7) and 51 mg of PTA (obtained in Synthesis Example 1) were sequentially added 2.11 ml of DMF and 0.90 ml of ethyleneglycol for dissolution under an atmosphere of nitrogen. To the resulting solution was added dropwise 4.21 ml of cyclohexanol (heated to 50° C.). After stirring and cooling to room temperature, there was obtained a transparent yellowish greenish brown varnish. This varnish gave no precipitates even after cooling to −25° C.

Example 20

To a mixture of 115 mg of BDSP-2 (obtained in Example 9) and 51 mg of PTA (obtained in Synthesis Example 1) were sequentially added 1.70 ml of DMF and 0.49 ml of ethyleneglycol for dissolution under an atmosphere of nitrogen. To the resulting solution was added dropwise 5.11 ml of cyclohexanol (heated to 50° C.). After stirring and cooling to room temperature, there was obtained a transparent light green varnish. This varnish gave no precipitates even after cooling to −25° C.

The samples of varnish obtained in Examples 11 to 20 were tested for viscosity by using an E-type viscometer (ELD-50, made by Tokyo Keiki). The results are shown in Table 1.

Example 21

Each sample of varnish obtained in Examples 10 to 20 was applied by spin coating to an ITO substrate which had undergone ozone cleaning for 40 minutes immediately before use. The coating step was followed by baking. Thus there was obtained a charge transporting thin film. The resulting charge transporting thin film was found to be amorphous solid, and it did not crystallize after standing at room temperature and 50% RH for 7 days. Table 1 shows the baking condition, film thickness, and ionization potential ($I_p$ for short hereinafter).

Each sample of charge transporting thin film produced from the varnish in Examples 10 and 14 was placed in a vacuum chamber and coated with Al (100 nm thick) by vacuum deposition. The resulting device was tested for conductivity. The results are shown in Table 1.

It is noted from Table 1 that the thin film produced from the varnish in Examples 10 and 14 gave high conductivity even after baking at 180° C. for 2 hours.

Incidentally, the film thickness, $I_p$ value, and conductivity were measured by using the following apparatus.

(1) Film thickness:
  Surface shape measuring apparatus (DEKTAK3ST, made by Nippon Shinku Gijutu)
(2) $I_p$ value:
  Photoelectron spectrometer (AC-2, made by Riken Keiki)
(3) Conductivity:
  Semiconductor parameter analyzer (4156C, Agilent Technologies), which was used to measure voltage and current.

Example 22

An ITO substrate was coated with a hole transporting thin film by the method mentioned in Example 21. Then it was coated sequentially with α-NPD, Alq$_3$, LiF, and Al by vapor deposition in a vacuum chamber. Their film thickness is 40 nm, 60 nm, 0.5 nm, and 100 nm, respectively. Vacuum deposition was performed at a pressure below $8 \times 10^{-4}$ Pa. The rate of deposition was 0.02 to 0.04 nm/s for LiF and 0.3 to 0.4 nm/s for other components. The substrate was transferred from one station to another in vacuum. The thus obtained OLED device has the characteristic properties as shown in Table 2.

It is noted from Table 2 that the OLED device with a hole transporting thin film formed from the varnish in Examples 10 to 13 and 15 to 20 is superior to the OLED device without such a hole transporting thin film in having a reduced driving voltage and an increased light emitting efficiency and maximum luminance. In addition, it has a uniform emitting surface free of dark spots.

Incidentally, the EL characteristic properties were measured by using the following apparatus.
(1) EL measuring system: Emission quantum efficiency measuring apparatus (EL1003, made by Precise Gauge)
(2) Voltage indicator (voltage generator): Programmable DC voltage/current source (R6145, made by Advantest)
(3) Ammeter: Digital multimeter (R6581D, made by Advantest)
(4) Luminance meter: LS-110 (made by Minolta)

Comparative Example 1

An ITO substrate which had undergone ozone cleaning for 40 minutes immediately before use was coated sequentially with α-NPD, Alq$_3$, LiF, and Al by vapor deposition in a vacuum chamber in the same way as mentioned in Example 21. The thus obtained OLED device was tested for characteristic properties in the same way as mentioned above. The results are shown in Table 2.

Comparative Example 2

To a mixture of 206 mg of (+)-10-camphorsulfonic acid and 100 mg of PTA (obtained in Synthesis Example 1) was added 1.87 ml of DMAc for dissolution under an atmosphere of nitrogen. To the resulting solution was added 5.53 ml of cyclohexanol. After stirring at room temperature, there was obtained a transparent green varnish.

This varnish was made into a charge transporting thin film by the method mentioned in Example 21. The resulting charge transporting thin film was amorphous solid. Then, an OLED device was prepared by the method mentioned in Example 22.

Table 1 shows the viscosity of the varnish (measured by using the above-mentioned apparatus), the baking conditions, the film thickness, and the $I_p$ value. Table 2 shows the characteristic properties of the OLED device.

TABLE 1

| Varnish | Solids (mass %) | Viscosity (mPa·s) | Baking conditions | Film thickness (nm) | Conductivity (S/cm) | $I_p$ value |
|---|---|---|---|---|---|---|
| Example 10 | 2.4 | — | 180° C., 2 h | 14 | $1.9 \times 10^{-7}$ | — |
| Example 11 | 4.1 | 1.1 | 180° C., 2 h | 24 | — | 5.57 |
| Example 12 | 4.3 | 1.1 | 180° C., 2 h | 24 | — | 5.78 |
| Example 13 | 2.9 | 1.0 | 140° C., 2 h | 14 | — | 5.62 |
| Example 14 | 4.3 | 10.7 | 180° C., 2 h | 86 | $4.6 \times 10^{-7}$ | 5.79 |
| Example 15 | 2.2 | 9.0 | 220° C., 15 min | 25 | — | 5.72 |
| Example 16 | 2.9 | 10.3 | 180° C., 15 min | 39 | — | 5.62 |
| Comparative Example 2 | 4.2 | 11.5 | 140° C., 2 h | 24 | — | 5.47 |
| Comparative Example 2 | 4.2 | 11.5 | 180° C., 2 h | 12 | — | 5.49 |
| Example 17 | 2.4 | 9.0 | 220° C., 15 min | 17 | — | 5.84 |
| Example 18 | 2.8 | 9.3 | 220° C., 15 min | 26 | — | 5.72 |
| Example 19 | 2.8 | 9.3 | 220° C., 15 min | 24 | — | 5.75 |
| Example 20 | 2.3 | 9.0 | 220° C., 15 min | 17 | — | 5.76 |

TABLE 2

| Varnish | Film thickness (nm) | Current density (mA/cm$^2$) | Voltage (V) | Luminance (cd/m$^2$) | Current efficiency (cd/A) | Emission starting voltage (V) | Maximum luminance (cd/m$^2$) |
|---|---|---|---|---|---|---|---|
| Example 10 | 14 | 0.498 | 7.0 | 10.1 | 2.04 | 2.75 | 10410 |
| Example 11 | 24 | 10.2 | 7.0 | 376 | 3.68 | 2.75 | 12460 |
| Example 12 | 24 | 33.5 | 7.0 | 1194 | 3.56 | 2.75 | 19420 |
| Example 13 | 14 | 23.1 | 7.0 | 856 | 3.71 | 2.75 | 26500 |
| Example 14 | 25 | 44.1 | 7.0 | 2127 | 4.80 | 2.50 | 24770 |
| Example 15 | 39 | 12.1 | 7.0 | 392 | 3.24 | 2.75 | 20600 |
| Example 16 | 17 | 237 | 7.0 | 9001 | 3.84 | 2.50 | 18300 |
| Example 17 | 26 | 190 | 7.0 | 9344 | 4.92 | 2.50 | 22490 |

TABLE 2-continued

| Varnish | Film thickness (nm) | Current density (mA/cm$^2$) | Voltage (V) | Luminance (cd/m$^2$) | Current efficiency (cd/A) | Emission starting voltage (V) | Maximum luminance (cd/m$^2$) |
|---|---|---|---|---|---|---|---|
| Example 19 | 24 | 137 | 7.0 | 7082 | 5.18 | 2.50 | 26630 |
| Example 20 | 17 | 233 | 7.0 | 10570 | 4.37 | 2.50 | 19210 |
| Comparative Example 1 | — | 10 | 9.2 | 330 | 3.3 | 4.50 | 10640 |
| Comparative Example 1 | — | 0.37 | 7.0 | 1.2 | 0.32 | 4.50 | 10640 |
| Comparative Example 2 | 24 | 0.419 | 7.0 | 8.89 | 2.12 | 4.00 | 5540 |
| Comparative Example 2 | 12 | 10 | 10.2 | 239 | 2.39 | 6.50 | 4410 |

The invention claimed is:

1. A 1,4-benzodioxanesulfonic acid compound represented by formula (1), a 1,4-benzodioxanesulfonic acid compound represented by formula (2), a 1,4-benzodioxanesulfonic acid compound having the repeating unit represented by formula (3), or a 1,4-benzodioxanesulfonic acid compound having the repeating unit represented by formula (4)

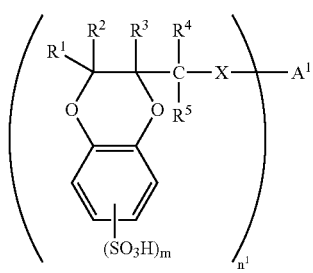

[where $R^1$ to $R^5$ each independently denotes a hydrogen atom, an unsubstituted or substituted monovalent hydrocarbon group, or a halogen atom; X denotes a single bond, O, S, or NH; $A^1$ denotes a hydrogen atom, a halogen atom (if X denotes a single bond), S (if X denotes a single bond), S(O) group, S(O$_2$) group, any of N, Si, P, and P(O) group having an unsubstituted or substituted group binding thereto, an unsubstituted or substituted hydrocarbon group, 1,3,5-triazine group, or a substituted or unsubstituted group represented by formula (5) or (6)

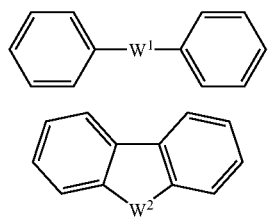

(where $W^1$ and $W^2$ each independently denotes O, S, S(O) group, S(O$_2$) group, or any of N, Si, P, and P(O) group having an unsubstituted or substituted group binding thereto); $n^1$ is an integer which equals the valence of $A^1$ and satisfies $1 \leq n^1$; and m denotes the number of sulfonic acid groups binding to the benzene ring of the 1,4-benzodioxane skeleton, with $1 \leq m \leq 4$]

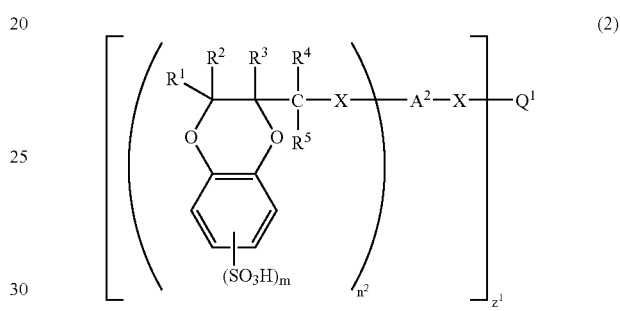

(where $R^1$ to $R^5$, X, and m are defined as above; $A^2$ denotes an unsubstituted or substituted divalent or higher multivalent hydrocarbon group, a divalent or trivalent 1,3,5-triazine group, or a substituted or unsubstituted group represented by the formula (5) or (6) above; $Q^1$ denotes a hydrogen atom, a halogen atom (if X denotes a single bond), S (if X denotes a single bond), S(O) group, S(O$_2$) group, any of N, Si, P, and P(O) group having an unsubstituted or substituted group binding thereto, an unsubstituted or substituted hydrocarbon group, 1,3,5-triazine group, or a substituted or unsubstituted group represented by the formula (5) or (6) above; $n^2$ is an integer which equals the number of valence of $A^2$ minus 1 and satisfies $1 \leq n^2$; and $z^1$ is an integer which equals the number of valence of $Q^1$ and satisfies $1 \leq z^1$)

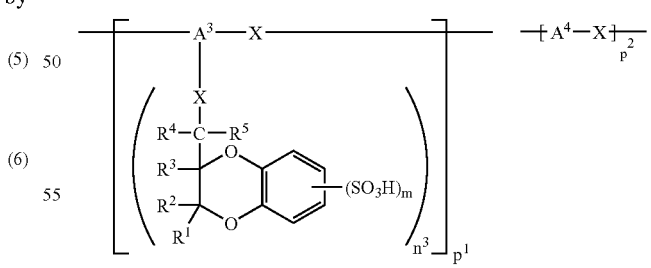

(where $R^1$ to $R^5$, X, and m are defined as above; $A^3$ denotes an unsubstituted or substituted trivalent or higher multivalent hydrocarbon group, a trivalent 1,3,5-triazine group, or a substituted or unsubstituted group represented by the formula (5) or (6) above; $A^4$ denotes an unsubstituted or substituted divalent or higher multivalent hydrocarbon group, a divalent or trivalent 1,3,5-triazine group, or a substituted or unsubstituted group represented by the formula (5) or (6) above; $n^3$ is an integer which equals the number of valence of $A^3$ minus 2 and satisfies $1 \leq n^3$; and $p^1$ is an integer which satisfies $1 \leq p^1$ and $p^2$ is an integer which satisfies $0 \leq p^2$, with $1 \leq p^1 + p^2 \leq 10000$)

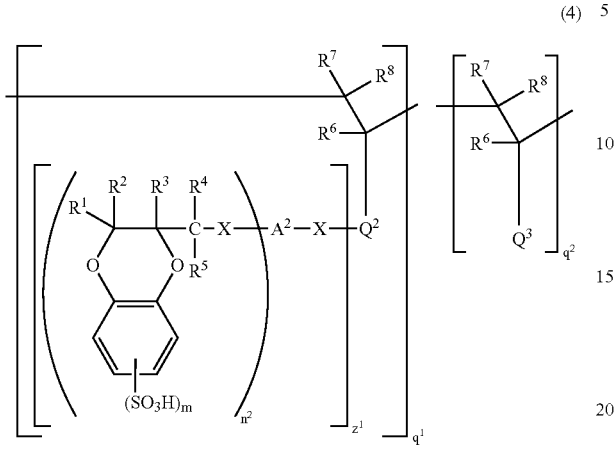

(where $R^1$ to $R^5$, $A^2$, X, m, and $n^2$ are defined as above; $R^6$ to $R^8$ each independently denotes a hydrogen atom, an unsubstituted or substituted monovalent hydrocarbon group, or a halogen atom; $Q^2$ denotes an unsubstituted or substituted divalent or higher multivalent hydrocarbon group, a divalent or trivalent 1,3,5-triazine group, or a substituted or unsubstituted group represented by the formula (5) or (6) above; $Q^3$ denotes an unsubstituted or substituted hydrocarbon group, a 1,3,5-triazine group, or a substituted or unsubstituted group represented by the formula (5) or (6) above; $z^2$ is an integer which equals the number of valence of $Q^2$ minus 1 and satisfies $1 \leq z^2$; and $q^1$ is an integer which satisfies $1 \leq q^1$ and $q^2$ is an integer which satisfies $0 \leq q^2$, with $1 \leq q^1 + q^2 \leq 10000$.)

2. An electron acceptor substance composed of the 1,4-benzodioxanesulfonic acid compound as defined in claim 1.

3. A charge transporting varnish comprising the 1,4-benzodioxanesulfonic acid compound as defined in claim 1, a charge transporting substance, and a solvent.

4. A charge transporting thin film comprising the 1,4-benzodioxanesulfonic acid compound as defined in claim 1 and a charge transporting substance.

5. An organic electroluminescence device having the charge transporting thin film as defined in claim 4.

6. A process which comprises reacting (o-dihydroxybenzene)sulfonic acid represented by formula (7)

(7)

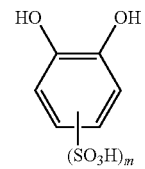

(where m denotes the number of sulfonic acid groups binding to the dihydroxybenzene ring, with $1 \leq m \leq 4$)
with an epihalohydrin compound represented by formula (8)

(8)

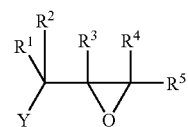

(where $R^1$ to $R^5$ each independently denotes a hydrogen atom, an unsubstituted or substituted monovalent hydrocarbon group, or a halogen atom; and Y denotes a halogen atom)
in the presence of a catalyst, thereby producing a 1,4-benzodioxanesulfonic acid compound represented by formula (9)

(9)

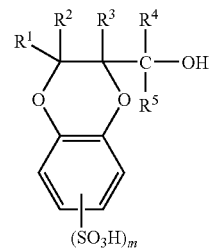

(where $R^1$ to $R^5$ and m are defined as above.)

* * * * *